(12) United States Patent
Kenny et al.

(10) Patent No.: US 10,932,952 B2
(45) Date of Patent: Mar. 2, 2021

(54) DRY BIOCOMPATIBLE DISINTEGRATABLE FILMS FOR DELIVERING PARTICULATE EGG SHELL MEMBRANE TO A WOUND

(71) Applicant: BIOVOTEC AS, Oslo (NO)

(72) Inventors: Enda Kenny, Dublin (IE); Ralf Schmidt, Nesbru (NO); Henri-Pierre Suso, Oslo (NO); Paul Barham, Dublin (IE)

(73) Assignee: BIOVOTEC AS, Oslo (NO)

( * ) Notice: Subject to any disclaimer, the term of this patent is extended or adjusted under 35 U.S.C. 154(b) by 0 days.

(21) Appl. No.: 15/774,665

(22) PCT Filed: Nov. 11, 2016

(86) PCT No.: PCT/EP2016/077443
§ 371 (c)(1),
(2) Date: May 9, 2018

(87) PCT Pub. No.: WO2017/081259
PCT Pub. Date: May 18, 2017

(65) Prior Publication Data
US 2018/0325740 A1      Nov. 15, 2018

(30) Foreign Application Priority Data

Nov. 11, 2015   (GB) .................................... 1519923

(51) Int. Cl.
*A61F 13/00*           (2006.01)
*A61L 26/00*           (2006.01)
(Continued)

(52) U.S. Cl.
CPC ...... *A61F 13/00012* (2013.01); *A61K 31/717* (2013.01); *A61L 26/0023* (2013.01);
(Continued)

(58) Field of Classification Search
CPC ............ A61F 13/00012; A61K 31/717; A61K 9/0014; A61L 26/0023; A61L 26/0028;
(Continued)

(56) References Cited

U.S. PATENT DOCUMENTS 3,194,732 A    7/1965  Neuhauser
3,196,075 A *  7/1965  Neuhauser .............. A61L 15/40
                                             602/48
(Continued)

FOREIGN PATENT DOCUMENTS

BE     677335 A     9/1966
CA     721555 A    11/1965
(Continued)

OTHER PUBLICATIONS

Shinko et al. (JP2005194401 (A) English translation) hereinafter Shinko (Year: 2005).*
(Continued)

*Primary Examiner* — Robert A Wax
*Assistant Examiner* — Quanglong N Truong
(74) *Attorney, Agent, or Firm* — Cantor Colburn LLP

(57) ABSTRACT

The invention provides a dry biocompatible film comprising at least one film forming material and particulate egg shell membrane (ESM), wherein said particulate ESM is distributed substantially uniformly in and/or on the film and wherein said film, or portion thereof, disintegrates upon contact with a wound or an exudate thereof. The invention further provides methods for preparing the films of the invention and the uses thereof in methods to promote the healing of wounds.

23 Claims, 1 Drawing Sheet

US 10,932,952 B2

Page 2

(51) Int. Cl.
*A61K 31/717* (2006.01)
*A61K 9/00* (2006.01)
(52) U.S. Cl.
CPC ....... *A61L 26/0028* (2013.01); *A61L 26/0033* (2013.01); *A61L 26/0038* (2013.01); *A61L 26/0057* (2013.01); *A61K 9/0014* (2013.01)
(58) Field of Classification Search
CPC ............. A61L 26/0033; A61L 26/0057; A61L 26/0038
See application file for complete search history.

(56) References Cited

U.S. PATENT DOCUMENTS

| | | | |
|---|---|---|---|
| 3,400,199 | A | 9/1968 | Balassa |
| 3,558,771 | A * | 1/1971 | Balassa .................. A61L 15/40 424/581 |
| 3,804,949 | A | 4/1974 | Balassa |
| 5,356,614 | A | 10/1994 | Sharma |
| 5,503,847 | A | 4/1996 | Queen et al. |
| 6,201,164 | B1 | 3/2001 | Wulff et al. |
| 6,541,447 | B1 | 4/2003 | Dawson |
| 6,946,551 | B2 | 9/2005 | Long et al. |
| 7,767,297 | B2 | 8/2010 | Tajima et al. |
| 7,780,994 | B2 | 8/2010 | Lynn et al. |
| 8,173,174 | B2 | 5/2012 | Strohbehn et al. |
| 8,197,852 | B2 | 6/2012 | Strohbehn et al. |
| 8,197,853 | B2 | 6/2012 | Strohbehn et al. |
| 8,211,477 | B2 | 7/2012 | Strohbehn et al. |
| 8,425,943 | B2 | 4/2013 | Strohbehn et al. |
| 8,580,315 | B2 | 11/2013 | Devore et al. |
| 2004/0180025 | A1 | 9/2004 | Long et al. |
| 2004/0180851 | A1 | 9/2004 | Long et al. |
| 2005/0107302 | A1 | 5/2005 | Dawson |
| 2005/0246840 | A1 | 11/2005 | Sano et al. |
| 2006/0159816 | A1 | 7/2006 | Vlad |
| 2007/0178170 | A1 | 8/2007 | DeVore et al. |
| 2007/0225220 | A1 | 9/2007 | Ming et al. |
| 2008/0063677 | A1 | 3/2008 | Long et al. |
| 2008/0124381 | A1 | 5/2008 | Barnhart et al. |
| 2008/0146869 | A1 | 6/2008 | Chow et al. |
| 2009/0031691 | A1 | 2/2009 | Tajima et al. |
| 2009/0074879 | A1 | 3/2009 | Braguti |
| 2009/0104173 | A1 | 4/2009 | Strohbehn et al. |
| 2009/0206009 | A1 | 8/2009 | Floh et al. |
| 2010/0254961 | A1 | 10/2010 | Nishio et al. |
| 2010/0266646 | A1 | 10/2010 | Dvorak et al. |
| 2011/0150961 | A1 | 6/2011 | Perry et al. |
| 2013/0035473 | A1 | 2/2013 | Summers et al. |
| 2013/0337080 | A1 | 12/2013 | Wedekind et al. |
| 2013/0344129 | A1 | 12/2013 | Washburn et al. |
| 2014/0294961 | A1 | 10/2014 | Kato et al. |
| 2014/0348939 | A1 | 11/2014 | Blaine et al. |
| 2017/0319629 | A1 | 11/2017 | Schmidt et al. |
| 2020/0030492 | A1 | 1/2020 | Kenny et al. |

FOREIGN PATENT DOCUMENTS

| | | |
|---|---|---|
| CN | 1295848 A | 5/2001 |
| CN | 1432592 A | 7/2003 |
| CN | 1569244 A | 1/2005 |
| CN | 101288669 A | 10/2008 |
| CN | 101317965 A | 12/2008 |
| CN | 101439114 A | 5/2009 |
| CN | 101575771 A | 11/2009 |
| CN | 101697815 A | 4/2010 |
| CN | 101822783 A | 9/2010 |
| CN | 101837094 A | 9/2010 |
| CN | 102517363 A | 6/2012 |
| CN | 103275205 A | 9/2013 |
| CN | 103300357 A | 9/2013 |
| EP | 2020455 A2 | 2/2009 |
| FR | 1348353 A | 1/1964 |
| FR | 2035769 A1 | 12/1970 |
| GB | 949946 | 2/1964 |
| GB | 1251720 | 10/1971 |
| IN | 00315DE2006 A | 8/2007 |
| IN | 01957MU2008 | 3/2010 |
| JP | 63309273 A | 12/1988 |
| JP | 2231426 A | 9/1990 |
| JP | H02231426 A | 9/1990 |
| JP | 5015581 A | 1/1993 |
| JP | 6192443 A | 7/1994 |
| JP | 7138142 A | 5/1995 |
| JP | 7277949 A | 10/1995 |
| JP | 9241146 A | 9/1997 |
| JP | 11228438 A | 8/1999 |
| JP | 2002212069 A | 7/2002 |
| JP | 2002249440 A | 9/2002 |
| JP | 2002265350 A | 9/2002 |
| JP | 2003225298 A | 8/2003 |
| JP | 2003246741 A | 9/2003 |
| JP | 2004018471 A | 1/2004 |
| JP | 2006069892 A | 3/2006 |
| JP | 3814247 B2 | 8/2006 |
| JP | 2006326018 A | 12/2006 |
| JP | 2007197393 A | 8/2007 |
| JP | 2008007419 A | 1/2008 |
| JP | 4187976 B2 | 11/2008 |
| JP | 2009089858 A | 4/2009 |
| JP | 2013040115 A | 2/2013 |
| JP | 05212514 B2 | 6/2013 |
| JP | 2013216652 A | 10/2013 |
| KR | 20130103406 A | 9/2013 |
| TR | 201006790 A2 | 12/2010 |
| WO | 9951175 A1 | 10/1999 |
| WO | 200170194 A1 | 9/2001 |
| WO | 2004080388 A2 | 9/2004 |
| WO | 2004080428 A2 | 9/2004 |
| WO | 2005023176 A2 | 3/2005 |
| WO | 2005039499 A2 | 5/2005 |
| WO | 2005040228 A2 | 5/2005 |
| WO | 2005107774 A1 | 11/2005 |
| WO | 2009048924 A1 | 4/2009 |
| WO | 2010006260 A1 | 1/2010 |
| WO | 2010086616 A1 | 8/2010 |
| WO | 2010122490 A2 | 10/2010 |
| WO | 2012036645 A2 | 3/2012 |
| WO | 2012112410 A2 | 8/2012 |
| WO | 2014028327 A1 | 2/2014 |
| WO | 2014190227 A1 | 11/2014 |
| WO | 2015009256 A1 | 1/2015 |
| WO | 2015058790 A1 | 4/2015 |
| WO | 2016066718 A1 | 5/2016 |

OTHER PUBLICATIONS

Cordeiro et al.; "Recent Patents on Eggshell: Shell and Membrane Applications"; Recent Patents on Food, Nutritiion & Agriculture; 3; pp. 1-8; (2011).

Ruff et al.; "Eggshell Membrans: A Possible New Natural Therapeutic for Joint and Connective Tissue Disorders. Results from Two Open-Label Human Clinical Studies"; Clinical Interventions in Aging; 4; pp. 235-240; (2009).

Ruff et al.; "Safety Evaluation of a Natural Eggshell Membrane-Derived Product"; Food and Chemical Toxicology; 50; pp. 604-611; (2012).

Benson et al.; "Effects of Natural Eggshell Membrane (NEM) on Cytokine Production in Cultures of Peripheral Blood Mononuclear Cells: Increased Suppression of Tumor Necrosis Factor-Alpha Levels After In Vitro Digestion"; J. Med Food; 14(4); pp. 360-368; (2012).

Gibson et al.; "MMPs Made Easy"; Wounds International; 1(1); pp. 1-6; (2009) available from http://www.woundsinternational.com.

Holmes et al.; "Collagen-Based Wound Dressings for the Treatment of Diabetes-Related Foot Ulcers: a Systematic Review"; Diabetes, Metabolic Syndrome and Obesity: Targets and Therapy; 6; pp. 17-29; (2013).

Kim et al.; "Coaxially Electrospun Micro / Nanofibrous Poly(E-caprolactone) / Eggshell-Protein Scaffold"; Bioninsp. Biomim.; 3; 9 pages; stacks.iop.org/BB/016006; (2008).

(56) References Cited

OTHER PUBLICATIONS

Mishra et al.; "Manufacturing Techniques of Orally Dissolving Films"; Pharmaceutical Technology; 35(1); pp. 1-4; (2011).
O'Brien, Fergal J., "Influence of Freezing Rate on Pore Structure in Freeze-dried Collagen-GAG Scaffolds"; Biomaterials; 25(6); pp. 1077-1086; (2004).
O'Brien, Fergal J.; "The Effect of Pore Size on Cell Adhesion in Collagen-GAG Scaffolds"; Biomaterials; 26(4); pp. 433-441; (2005).
Ohto-Fujita et al.; "Hydrolyzed Eggshell Membrane Immobilized on Phosphorylcholine Polymer Supplies Extracellular Matrix Environment for Human Dermal Fibroblasts"; Cell Tissue Res; 345; pp. 177-190; (2011).
Qin, Yimin; "Review_Aliginate Fibres: An Overview of the Production Processes and Applications in Wound Management"; Polymer International; 57; pp. 171-180; (2008).
Ruff et al.; "Reduction of Pro-Inflammatory Cytokines in Rats Following 7-day Oral Supplementation with a Proprietary Eggshell Membrane-Derived Product"; Modern Research in Inflammation; 3(1); pp. 19-25; (2014).
Tan et al.; "A Scanning and Transmission Electron Microscopic Study of the Membranes of Chicken Egg"; Histol Histopath; 7; pp. 339-345; (1992).
World Union of Wound Healing Societies (WUWHS); Principles of Best Practice: Wound Infection in Clinical Practice; An International Consensus; London: MEP Ltd; 12 Pages; (2008) Available from www.mepltd.co.uk.
Yi et al.; "Soluble Eggshell Membrane Protein: Preparation, Characterization and Biocompatibility"; Biomaterials; 25; pp. 4591-4599; (2004).
Balaz, Matej; "Eggshell Membrane Biomaterial as a Platform for Applications in Materials Science"; Acta Biomaterialia; 10; pp. 3827-3843; (2014).
Chen et al.; "Preparation and Characterization of Polyurethane/ soluble Eggshell Membrane Nanofibers"; Bio-Medical Materials and Engineering; 24; pp. 1979-1989; (2014).
CN101317965 A English Abstract; Sep. 23, 2015; 1 page.
Eming et al.; "Inflammation in Wound Repair: Molecular and Cellular Mechanisms"; Journal of Investigative Dermatology; 127; pp. 514-525; (2007).
Hwang et al.; "Poly(ethylene glycol) Cryogels as Potential Cell Scaffolds: Effect of Polymerization Conditions on Cryogel Microstructure and Properties"; J. Mater Chem.; 20; pp. 345-351; (2010).
International Search Report and Written Opinion; International Application No. PCT/EP2016/077443; International Filing Date Nov. 11, 2016; dated Feb. 20, 2017; 11 pages.
Johnson, et al.; "Randomized, Controlled Trial of Topical Exit-Site Application of Honey (Medihoney) versus Mupirocin for the Prevention of Catheter-Associated Infections in Hemodialysis Patients"; J Am Soc Nephrol; 16; pp. 1456-1462; (2005).
JPH02231426 A English Asbstract; 1 page; Sep. 23, 2015.
Loh et al.; "Three-Dimensional Scaffolds for Tissue Engineering Applications: Role of Porosity and Pore Size"; Tissue Engineering: Part B, 19(6); pp. 485-501; (2013).
Murphy et al.; "Understanding the Effect of Mean Pore Size on Cello Activity in Collagen-glycosaminoglycan Scaffolds"; Cell Adhesion & Migration; 4:3; pp. 377-381; (2010).
Ratanavaraporn et al.; "Effects of Acid Type on Physical and Biological Properties of Collagen Scaffolds"; J. Biomater Sci. Polymer Edn., 19(7); pp. 945-952; (2008).
Yang et al.; "Egg Membrane as a New Biological Dressing in Split-Thickness Skin Graft Donor Sites: A Preliminary Clinical Evaluation"; Chang Gung Med J; 26(3); pp. 153-158; (2003).
Yannas et al.; "Synthesis and Characterization of a Model Extracellular Matrix that Induces Partial Regeneration of Adult Mammalian Skin"; Proc. Natl. Acad. Sci. USA; 86; pp. 933-937; (1989).
Feng Yl et al.; "Soluble Eggshell Mebrane Protein: Antibacterial Property and Biodegradability"; Journal of Wuhan University of Technology-Mater. Sci. Ed.; Sum. 75, vol. 22, No. 1, pp. 117-119; (2007).
Park, J. et al.; "Evaluation of bone healing with eggshell-derived bone graft substitutes in rat calvaria: A pilot study"; Journal of Biomedical Materials Research, vol. 87, Issue No. 1; 2008; pp. 203-214.
Sharma, A. et al.; "Efficacy of supermacroporous poly(ethylene glycol)-gelatin cryogel matrix for soft tissue engineering applications"; Materials Science and Engineering C, vol. 47; 2015; pp. 298-312.

* cited by examiner

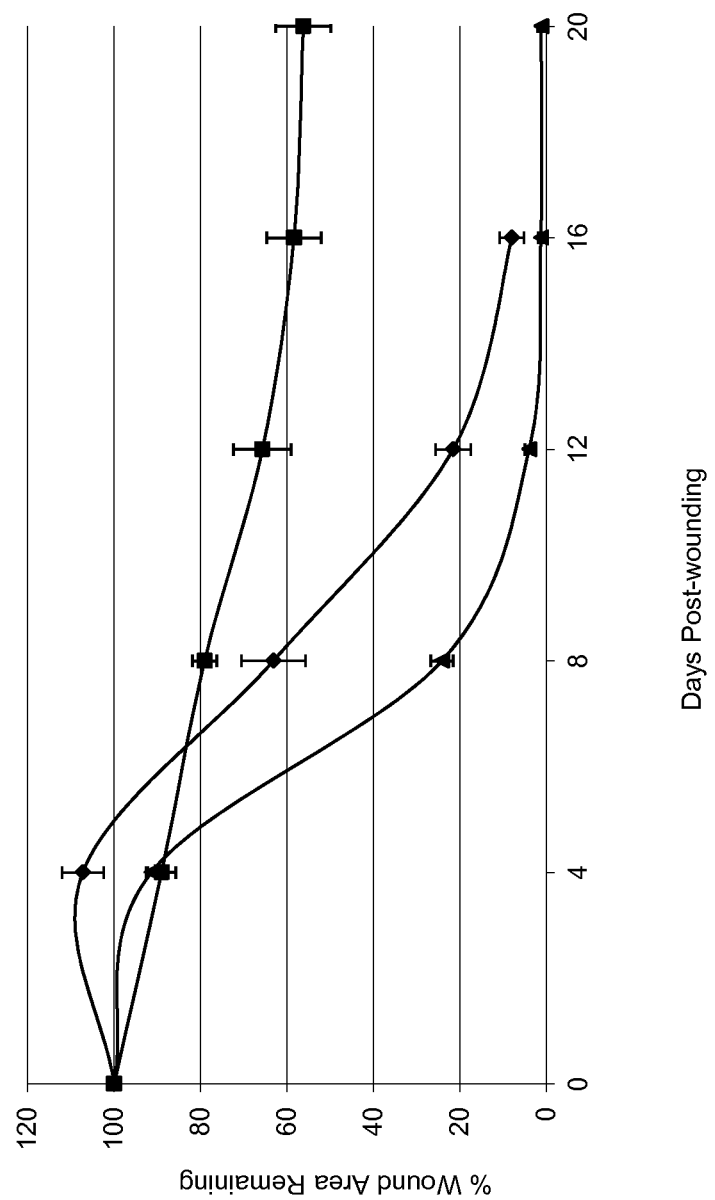

DRY BIOCOMPATIBLE DISINTEGRATABLE FILMS FOR DELIVERING PARTICULATE EGG SHELL MEMBRANE TO A WOUND

CROSS REFERENCE TO RELATED APPLICATIONS

This application is a National Stage application of PCT/EP2016/077443, filed Nov. 11, 2016, which claims the benefit of GB Application No. 1519923.5, filed Nov. 11, 2015, both of which are incorporated by reference in their entirety herein.

The present invention provides dry biocompatible films comprising particulate egg shell membrane (ESM) distributed substantially uniformly in and/or on the film which disintegrate upon contact with a wound or an exudate thereof and as such may act as a vehicle to deliver a substantially uniform amount of particulate ESM to a wound or part thereof. It has been recognised that particulate ESM is an effective wound healing agent when applied topically to the surface of a wound but, while the use of therapeutic agents in powder form is well established, the inventors have recognised that in the particular context of wound treatments this delivery form has a number of drawbacks. The inventors have therefore developed disintegratable (disintegrable) films comprising particulate ESM distributed substantially uniformly in and/or on the film as a novel and highly adaptable delivery platform capable of ensuring persistently uniform and reproducible delivery of a controllable amount of particulate ESM to wound surfaces of any orientation without appreciable transfer to other surfaces and wastage. The invention further provides composite wound dressings and implantable medical devices comprising such films and methods for manufacturing the same. The use of such films, wound dressings and implantable medical devices in the treatment of wounds in order to promote the healing thereof is also provided. As shown in the Examples, a disintegratable film comprising particulate ESM distributed substantially uniformly therein is capable of enhancing the healing of a surgical wound in a diabetic mouse model comparably to the active ingredient (recombinant platelet derived growth factor BB) of a currently widely used wound healing product.

Wounds, a breach in the integrity of, or denudement of, a tissue, commonly the skin, are an inevitable occurrence in the lives of humans and other animals. Wounds may be caused surgically, by physical injury (e.g. mechanical injuries; thermal injuries, for instance those resulting from excessive heat or cold; electrical injuries, for instance those caused by contact with sources of electrical potential; and radiation damage caused, for example, by prolonged, extensive exposure to infrared, ultraviolet or ionizing radiations) or by a spontaneously forming lesion such as a skin ulcer (e.g. a venous, diabetic or pressure ulcer), an anal fissure, a mouth ulcer and acne vulgaris.

In the medical fields, wounds are typically defined as either acute or chronic. Acute wounds are wounds that proceed orderly through the three recognised stages of the healing process following haemostasis (i.e. the inflammatory stage, the proliferative stage and the remodelling phase) without a protracted timecourse. Chronic wounds are defined as those which fail to heal or where there is excessive skin loss such as through burns. Such wounds do not complete the ordered sequence of biochemical events of the healing process because the wound becomes stalled in one of the healing stages. Commonly, chronic wounds are stalled in the inflammatory phase. Chronic wounds are a major source of morbidity for patients.

The primary goal of wound healing treatments is to close or reform the outer layers of the wounded tissue, e.g. the epidermis in the context of a skin wound, so as to prevent blood loss or infection of the underlying tissues. For acute wounds this can be relatively straightforward with treatment placing great reliance on the natural healing processes of the wounded subject. However, in the case of chronic wounds, those healing processes are not functioning as they should and so a key goal in their treatment is to enhance and augment the response of the body and to assist the body in regeneration of damaged or broken tissues.

Conventional wound healing treatments focus on the haemostasis stage, absorption of excess exudate and maintenance of a sterile barrier to prevent infection whilst the skin lesion heals. Conventional products may also assist in maintaining topical pharmacological products in situ such as antibiotic and steroid creams and prevent them from being eroded from contact with clothing etc. Advanced wound healing products may share these features also, but their primary role is the maintenance of a moist healing environment. For optimal wound healing, it is critical that the wound bed is moist but not overly wet which will result in maceration of the surrounding skin as well as the wound bed. Advanced wound-care products may also contain pharmacological products to assist wound healing such as antibiotics or growth factors.

However, a major reason for development of chronic wounds is an imbalance in the wound repair cycle following haemostasis and these prior art approaches do not focus on those other healing stages specifically, i.e. the inflammation, proliferation and tissue remodelling (e.g. re-epithelialisation) stages.

As such, a wound healing treatment which is able to deal with an excessive inflammatory response in the wound would be advantageous. Moreover, it has recently been shown that imbalances in the healing process during the inflammatory phase can lead to overproduction and/or overactivity of proteases, e.g. MMPs (e.g. MMP-2, MMP-8 and MMP-9), collagenase, elastase and plasmin in the wound bed. This leads to destruction of newly synthesized extracellular matrix (ECM) and destruction of endogenously produced growth and differentiation factors within the wound bed. This imbalance can be addressed by the addition of stimulatory growth factors such as Regranex™ (recombinant human PDGF), however, even in this case the exogenous PDGF can be quickly inactivated by proteases. Another way this can be addressed is through the addition of proteins or other materials which preferentially bind the proteases and divert them from proteolysis of the ECM constituents and protein growth factors such as PDGF. Such products include collagen based materials such as Promogran™ and complex ECM based materials such as porcine small intestine sub-mucosa (Oasis™). However, these products are derived from a mammalian source, usually bovine or porcine and are at risk from transfer of certain viruses or TSEs. Accordingly, a non-mammalian source would be preferable.

Recently, it has been shown that intact hen eggshell membrane (ESM) can be used to promote wound healing when placed as an intact film over damaged skin (Yang, J-Y et al. 2003. Chang Gung Med J).

ESM is a complex bi-layered protein-rich fibrous structure found in an avian egg between the albumen and the eggshell. Studies have shown that such membranes contain approximately 90% protein by weight (including collagen, elastin, fibronectin peptide growth factors, ovotrasferrin, lysl oxidase and lysozyme) and desmosine, isodesmosine and glycosaminoglycans (e.g. dermatane sulphate, chondroitin sulphate and hyaluronic acid). ESM can readily be separated from the eggshell and the internal components of the egg by a variety of mechanical means to produce an essentially pure preparation of ESM.

When placed as an intact sheet over a skin wound ESM functions as a semi-permeable membrane and allows moisture vapour transmission and so manages moisture within the wound bed. Its characteristics are similar to synthetic materials such as Biobrane™. However, intact ESM in sizes that are appropriate for use in wound healing contexts is difficult to prepare in commercially viable amounts. Intact ESM requires manual preparation to maintain a useable size and even then it would need to be applied as a mosaic of individual membranes. During processing the delicate material requires separation from residual bound calcium and associated egg white components and either aseptic processing or terminal sterilisation. Process and quality control sufficient for manufacture of a medical product in such contexts are, as a result, not technically or economically feasible.

Powders of ESM of 100-500 µm have also been proposed for the treatment of certain wounds via a topical route of administration (WO 2004/080428). The basis for this proposal is not clear and nor is evidence of successful treatment provided.

Powders of ESM of 100-500 µm have also been proposed for the treatment of pain and inflammation associated with arthritis and other inflammatory conditions via a systemic, in particular oral, route of administration (U.S. Pat. No. 8,580, 315).

Smaller ESM particles have been described and suggested for use in treatments for acute skin wounds and as replacement skin grafts for fresh wounds (U.S. Pat. Nos. 3,196,075 and 3,194,732). Any effects on the inflammatory phase of a chronic wound are not disclosed and a utility in the context of chronic wounds is not suggested.

The inventors have now found that that micronized ESM particles, in particular with an average particle diameter of less than 100 µm, have a particular repertoire of properties that make them especially advantageous in the treatment of chronic wounds, including burns, at risk of, or in which there is, (i) an inappropriate level of matrix-metalloproteinase (MMP) activity against ECM proteins and/or peptide growth or differentiation factors, in particular; and/or (ii) an excessive inflammatory response in order to promote healing thereof (PCT/EP2015/075041 (WO2016/066718); the contents of which are incorporated by reference in their entirety).

These properties include (i) the ability to reduce the degradation of ECM and/or peptide growth or differentiation factors in a wound, e.g. by reducing the activity of MMPs in a wound against ECM proteins and/or peptide growth or differentiation factors; (ii) an anti-inflammatory effect; (iii) an antimicrobial effect; (iv) the ability to promote the de novo formation of tissue by promoting migration of the cells of the wound tissue into the wound and/or the proliferation and/or differentiation of those cells e.g. through an ability to act as a scaffold for those cells; and (v) the ability not to interfere with the maintenance of a moist healing environment.

It is therefore clear that particulate ESM is an effective wound healing agent. However, while the use of therapeutic agents in powder form is well established, the inventors have recognised that in the particular context of wound treatments the delivery of this apparently simple agent is beset with a number of problems and conventional delivery vehicles have a number of practical disadvantages.

Particulate ESM can potentially be applied directly to the wound as a powder. The use of powder in the clinical setting is well established. However, containment of the powder at the wound site is difficult along with application of a powder to a vertical or inverted surface. In addition, the powder may contaminate the hands of the clinician and may be easily transferred to other surfaces which will require cleaning. Thus, the usability of a simple powder within a wound healing clinical environment is not optimum.

Particulate ESM can also be formulated with other materials such as gels for ease of handling which are then applied directly to the wound. A gel product is certainly easier to use than a powder and the gel product is certainly easier to contain within the wound bed, but it is difficult to apply a standard thickness of a liquid, e.g. aqueous, gel material across a wound without the use of an applicator. Thus, routine and uniform dosing across the wound surface is difficult. Moreover, the use of liquid gel formulations becomes challenging when application is to a vertical surface, such as the side of the leg for example in a venous leg ulcer, or an inverted surface most evidently because application of a liquid gel to a vertical or inverted surface may result in run-off before a secondary dressing can be applied to the wound. Less fluid gel formulations may be used but these are associated with their own problems of handling difficulties and non-uniform application.

Alternatively, particulate ESM may be coated onto or included in the wound contacting surface of a secondary dressing to form a multifunctional dressing which provides both an optimized wound bed and maintains the sterility barrier whilst managing moisture balance within the wound. However, wound types differ across different aetiologies and even with the same aetiology the characteristic of the wound may differ. For instance, venous leg ulcers may have a wide range of exudate properties, whereas diabetic foot ulcers may be much drier. Thus, while overall this approach can be employed to provide dressings suitable for a wide range of wound contexts, in practice, each arrangement of this type of dressing is specialised and so no single arrangement can be optimal in all wound scenarios. Indeed, a range of wound healing dressings is currently marketed to cope with these different aetiologies and physical characteristics. In addition, wounds may be infected and dressings used for such wound routinely incorporate antimicrobials such as elemental silver salts. Thus, in order for particulate ESM to be used routinely across a range of wound types in the form of a multifunctional dressing, many different product lines would be required, which payers and users may find challenging in terms of inventory management.

Thus, there is a need for a delivery method for particulate ESM in wound healing contexts such that the required particulate ESM dose may be applied evenly and reproducibly, across the entire wound surface if required, and which is adaptable enough to be used together with the range of existing wound dressings which provide moisture control and maintenance of a sterile mechanical barrier across the wound surface.

To address this need the inventors have developed dry biocompatible films comprising particulate ESM distributed substantially uniformly therein which disintegrate upon contact with a wound or an exudate thereof and as such may act as a vehicle to deliver a substantially uniform amount of particulate ESM to a wound or part thereof.

In a first aspect, the present invention therefore provides a dry biocompatible film comprising at least one film forming material and particulate egg shell membrane (ESM), wherein said particulate ESM is distributed substantially uniformly in and/or on the film and wherein said film, or portion thereof, disintegrates upon contact with a wound or an exudate thereof.

The film forming material is present in the film in an amount and in a form which permits the formation of a dry, biocompatible and disintegratable film (which formation may occur either in the presence of particulate ESM and/or other components of the film, or not, as context dictates). It should therefore be clear that the film forming material is essential to the structure of the film of the invention and thus performs that essential structural role (provides that essential contribution) either in combination with particulate ESM and/or other components of the film, or not, as contexts dictates.

References herein to film forming materials and the properties thereof are references to the materials which perform, or are intended primarily to perform, an essential structural role in the films of the invention and to the properties of such materials when used in or to prepare the films of the invention, i.e. when performing its essential structural role, unless context specifically dictates otherwise.

The film may be formed from (i.e. comprise) any film forming material (which terms includes "compound", "agent" and "molecule") or combination thereof which permits disintegration of the film upon contact with a wound or an exudate thereof. For the purposes on the present invention particulate ESM is not a "film forming material". The film forming material will be any material ("compound", "agent" or "molecule") which can be formed into a dry, disintegratable film which can carry or contain particulate ESM. In other embodiments the film forming material can be formed into a dry, disintegratable film in the presence of particulate ESM. In the present field of wound dressings, films are a form of dressing which is distinct from fibrous dressings (which include fabric, textile and paper dressings and the like) and so the film forming materials of use in the invention are not insoluble fibrous or filamentous materials.

Thus, the film may be a film which disintegrates in contact with moisture (water), i.e. the film, or at least the film forming material, is dissolvable in water and other aqueous liquids. In other words the film and/or the film forming materials are water-soluble.

Water soluble film forming materials can be considered to be compounds for which less than about 1000 parts pure water are required to solubilise 1 part of the film forming material, in particular when said compound is in the form of a film. In other embodiments less than about 500, e.g. less than about 250, 100, 50, 40, 30, 20, 10, 9, 8, 7, 6, 5, 4, 3, 2 or 1 parts pure water are required to solubilise 1 part of film forming material.

In other embodiments the film and/or the film forming material(s) may degrade and/or be degraded upon contact with other wound components, e.g. enzymes (for instance proteases (matrix metalloproteinases, plasmin, collagenase, elastase, chymase)), inflammatory/immune cells (e.g. macrophages, neutrophils, mast cells, and monocytes), wound cells, wounds microorganisms, salts, reactive oxygen species, the pH of the wound and the like. Degradation of the film forming materials in these contexts leads to the disruption/disintegration of the film.

Suitable film forming materials may be natural or synthetic and are typically polymers, in particular, polymer capable of forming flat lattice-like molecular arrangements, which may or may not involve covalent and/or ionic cross-linking. More specific examples include natural (fibrous) proteins and polysaccharides, e.g. those of the extracellular matrix (collagen (including all types and forms, preferably collagen I or gelatin), fibrin, keratin, elastin and glycosaminoglycans (e.g. hyaluronic acid, chondroitin sulfate, dermatan sulphate, keratan sulphate, heparin, heparan sulphate and hyaluronan)) and alginic acid, alginate, pectin, chitosan, pullulan, cellulose (all forms including oxidised regenerated cellulose, methylcellulose, carboxymethylcellulose, sodium carboxy methyl cellulose, hydroxyethylcellulose, hydroxypropylcellulose, hydroxypropylmethyl cellulose), xanthan gum, tragacanth gum, guar gum, acacia gum, arabic gum, carrageenan, amylose, amylopectin, dextrin, elsinan, zein, gluten, casein and fibronectin. Artificial film forming materials include polyvinyl alcohol (PVA), polyvinyl pyrrolidone (PVP), polyethylene glycol (PEG), polyacrylic acid (PAA), polylactic acid (PLA), polyglycolic acid (PGA), polycaprolactone (PCL), polydioxanone (PDS), poly(ethylene oxide terephthalate) (PEOT), poly(butylene terephthalate) (PBT), silicon nitride and copolymers thereof, e.g. polylactide-co-glycolide (PLAGA) and PEOT/PBT, methylmethacrylate copolymer, carboxyvinyl copolymers. Collagen (including all types and forms, preferably collagen I or gelatin) and cellulose (all forms including oxidised regenerated cellulose, methylcellulose, carboxymethylcellulose, hydroxypropylcellulose, hydroxyethylcellulose) are of note. Consistent with the above, when used in or to prepare the films of the invention, these film forming materials are not in insoluble fibrous or filamentous form. In certain embodiments the film does not contain an alginate.

Suitable film forming materials and films formed therefrom are described in WO 2005/039499, WO 2005/040228, WO 2009/048924 and WO 01/70194, the contents of which are incorporated by reference in their entirety.

Through the combination of different film-forming agents and varying the relative amounts thereof with one another and the particulate ESM, films with wide ranging physical characteristics, including pliability, wettability, adhesiveness, strength and rate of disintegration may be prepared and thus an optimised film may be prepared for a target wound. The rate of particulate ESM release (or, viewed alternatively, rate of film disintegration) may be controlled with careful selection of the type of film material and/or the molecular size of the film forming material. Indeed, even if a particular film forming material is used, e.g. a polysaccharide such as cellulose or pectin, by varying the proportions of different sized molecules of this compound in the in the film, varying release profiles can be achieved.

The creation of disintegratable films suitable for wounds which do not contain particulate ESM and the testing of their properties is well within the standard repertoire of the skilled artisan and so preparing the particulate ESM containing films of the invention of required characteristics should not prove unduly burdensome.

The term disintegrable may be used interchangeably with the term disintegratable.

Disintegration of the film of the invention may be defined as the loss of structural integrity of the film sufficient to release about 50% or more, e.g. about 60%, 70%, 80%, 90%, 95% or 99% or more, of the particulate ESM particles from the film in the area of disintegration (i.e. area in contact with the wound or exudate thereof). Disintegration of the film of the invention may also be defined as the loss of about 50% or more, e.g. about 60%, 70%, 80%, 90%, 95% or 99% or more, of the non-ESM material from the film in the area of disintegration.

Disintegration may manifest as the disruption of the macrostructure of the film sufficient to allow the ESM particles to disperse (be released) and/or the solubilisation of the film forming materials. Disruption may be of the individual film forming molecules themselves (intramolecular disruption) and/or any intermolecular interactions that may exist. Disruption in certain embodiments may involve the degradation (digestion) of the molecules of film forming materials or their intermolecular interactions by enzymes, cells or chemical attack (e.g. by reactive oxygen species, ions/salts and certain pH levels). In these embodiments the degradation products are not necessarily soluble in (may be dissolved into) the wound or exudate thereof. Solubilisation may result from the degradative action of the above mentioned mediators cleaving the molecules of film forming material into smaller, more soluble fragments, or by disrupting stabilising intermolecular interactions, or the molecules of film forming material being inherently dissolvable in a moist environment (i.e. water soluble).

In certain embodiments film disintegration may be essentially instantaneous upon contact with the wound or an exudate thereof, e.g. the parts of the film in contact with wound or exudate thereof disintegrate in less than about 180 seconds, e.g. less than about 150, 120, 90, 60 or 30 seconds. In other embodiments film disintegration may be rapid rather than instantaneous, e.g. the parts of the film in contact with wound or exudate thereof disintegrate in about 3 to about 25 minutes, e.g. about 3 to about 20, 18, 15, 12, 10, 8 or 5 mins, about 5 to about 25, 20, 18, 15, 12, 10 or 8 mins, about 8 to about 25, 20, 18, 15, 12 or 10 mins, about 10 to about 25, 20, 18, 15 or 12 mins, about 12 to about 25, 20, 18 or 15 mins, about 15 to about 25, 20 or 18 mins, about 18 to about 25 or 20 mins, or about 20 to about 25 mins. Any and all ranges derivable from the combination of any of these endpoint values are specifically contemplated.

In still further embodiments film disintegration may be slow rather than rapid or instantaneous, e.g. the parts of the film in contact with wound or exudate thereof disintegrate in about 25 to 180 minutes, e.g. about 25 to about 150, 120, 100, 80 or 50 mins, about 50 to about 180, 150, 120, 100 or 80 mins, about 80 to about 180, 150, 120 or 100 mins, about 100 to about 180, 150 or 120 mins, about 120 to about 180 or 150 mins, or about 150 to about 180 mins. Any and all ranges derivable from the combination of any of these endpoint values are specifically contemplated.

Disintegration times of about 5 to about 15 minutes may be convenient as this would permit repositioning of the film by the physician prior to disintegration and release of the particulate ESM and/or placement of additional dressing on top of the film.

Disintegration may be determined by any convenient means, e.g. using the test provided by (USP) 24, Disintegration <701>. Dissolution may be determined by any convenient means, e.g. using the test provided by (USP) 24, Dissolution <711>.

In certain embodiments the film comprises about 5% to about 95% w/w particulate ESM, e.g. about 5% to about 90%, 80%, 70%, 60%, 50%, 40%, 30%, 20% or 10%, e.g. about 10% to about 95%, 90% 80%, 70%, 60%, 50%, 40%, 30%, or 20% e.g. about 20% to about 95%, 90%, 80%, 70%, 60%, 50%, 40% or 30%, about 30% to about 95%, 90%, 80%, 70%, 60%, 50% or 40%, about 40% to about 95%, 90%, 80%, 70%, 60% or 50%, about 50% to about 90%, 80%, 70% or 60%, about 60% to about 95%, 90%, 80% or 70%, about 70% to about 95%, 90%, or 80%, about 80% to about 95% or 90% or about 90% to about 95% w/w particulate ESM, the remainder being made up of one or more film forming materials and optionally further excipients or active agents. Any and all ranges derivable from the combination of any of these endpoint values are specifically contemplated.

In certain embodiments the film comprises about 5% to about 95% w/w film forming materials, e.g. about 5% to about 90%, 80%, 70%, 60%, 50%, 40%, 30%, 20% or 10%, e.g. about 10% to about 95%, 90%, 80%, 70%, 60%, 50%, 40%, 30%, or 20% e.g. about 20% to about 95%, 90%, 80%, 70%, 60%, 50%, 40% or 30%, about 30% to about 95%, 90%, 80%, 70%, 60%, 50% or 40%, about 40% to about 95%, 90%, 80%, 70%, 60% or 50%, about 50% to about 95%, 90%, 80%, 70% or 60%, about 60% to about 95%, 90%, 80% or 70%, about 70% to about 95%, 90%, or 80%, about 80% to about 95%, or 90% or about 90% to about 95% w/w film forming materials, the remainder being made up of particulate ESM and optionally further excipients or active agents. Any and all ranges derivable from the combination of any of these endpoint values are specifically contemplated.

In other embodiments the film consists essentially of particulate ESM and film forming materials, e.g. at the percentage amounts recited above.

"% w/w" (or "percentage weight by weight") is a commonly used expression of the amount of a compound in a solid. 1% w/w equates to 1 gram of compound per 100 g of solid, 2% w/w equates to 2 g of compound per 100 g of solid, and so on.

Accordingly, % w/w may be expressed as g/100 g, grams per 100 grams and g 100 g$^{-1}$. 1% w/w also equates to 10 gram of compound per kilogram of solid. The skilled man would understand that through appropriate scaling calculations, % w/w can be expressed in terms of any SI unit of mass. Conversion into non-standard measures of concentration is also possible and would be routine to the skilled man. When referring to the contents of the films of the invention this is a reference to the dry weight of the film, i.e. in its essentially dry form.

In these embodiments it may be advantageous to provide the particulate ESM and the film forming material(s) at a ratio of about 1:19 to about 19:1, e.g. 1:10 to 10:1, 1:9 to 9:1, 1:8 to 8:1, 1:7 to 7:1, 1:6 to 6:1, 1:5 to 5:1, 1:4 to 4:1, 1:3 to 3:1, 1:2 to 2:1, or about 1:1, or 1:19 to 5:1, e.g. 1:19 to 1:1, 1:19 to 1:2, 1:19 to 1:3, 1:19 to 1:4, 1:19 to 1:5, 1:19 to 1:6, 1:19 to 1:7, 1:19 to 1:8, 1:19 to 1:9, 1:19 to 1:10, 1:10 to 5:1, 1:10 to 1:1, 1:10 to 1:2, 1:10 to 1:3, 1:10 to 1:4, 1:10 to 1:5, 1:10 to 1:6, 1:10 to 1:7, 1:10 to 1:8, 1:10 to 1:9, 1:9 to 1:1, 1:9 to 1:2, 1:9 to 1:3, 1:9 to 1:4, 1:9 to 1:5, 1:9 to 1:6, 1:9 to 1:7, 1:9 to 1:8, 1:8 to 1:1, 1:8 to 1:2, 1:8 to 1:3, 1:8 to 1:4, 1:8 to 1:5, 1:8 to 1:6, 1:8 to 1:7, 1:7 to 1:1, 1:7 to 1:2, 1:7 to 1:3, 1:7 to 1:4, 1:7 to 1:5, 1:7 to 1:6, 1:6 to 1:1, 1:6 to 1:2, 1:6 to 1:6, 1:6 to 1:4, 1:6 to 1:5, 1:5 to 1:1, 1:5 to 1:2, 1:5 to 1:3, 1:5 to 1:4, 1:4 to 1:1, 1:4 to 1:2, 1:4 to 1:3, 1:3 to 1:1, 1:3 to 1:2, or 1:1 to 1:2 (ESM:film forming material). Any and all ranges derivable from the combination of any of these endpoint values are specifically contemplated.

The use of film forming agents which have a history of use in wound healing products may be convenient. The use of compounds such as collagen and/or gelatin and soluble cellulose derivatives (e.g. hydroxypropylcellulose, hydroxyethylcellulose and carboxymethylcellulose) as the sole film forming material(s) is therefore especially preferred. The various ratios recited above apply mutatis mutandis to such embodiments.

In certain embodiments the film of the invention consists, or consists essentially, of particulate ESM and collagen and/or gelatin, preferably collagen. In these embodiments the ESM and collagen and/or gelatin are preferably present at ratios of 1:10 to 10:1 (ESM:collagen and/or gelatin), e.g. as recited above, preferably about 1:10, about 1:6, about 1:3, or about 1:1 i.e. about 10% w/w ESM to 90% w/w collagen and/or gelatin, about 15% ESM to 85% collagen and/or gelatin, about 25% ESM to 75% collagen and/or gelatin and about 50% ESM to 50% collagen and/or gelatin.

In other embodiments, the film of the invention consists, or consists essentially, of particulate ESM and soluble cellulose derivatives, preferably hydroxypropylcellulose, hydroxyethylcellulose and/or carboxymethylcellulose. In these embodiments the ESM and cellulose derivative are preferably present at ratios of 1:19 to 19:1 (ESM:cellulose derivative), e.g. as recited above, preferably about 1:9, about 1:6, about 1:3, or about 1:1, i.e. about 5% ESM to about 95% cellulose derivative, about 10% w/w ESM to 90% w/w cellulose derivative, about 15% ESM to 85% cellulose derivative, about 25% ESM to 75% c cellulose derivative and about 50% ESM to 50% cellulose derivative.

These films may additionally contain plasticisers, in particular those which are non-irritating for example urea, sucrose, sorbitol and glycerol. The plasticiser may be present at about 1% w/w to about 5% w/w, e.g. about 2% w/w to about 4% w/w, e.g. about 3% w/w, and in which case the above recited percentage will be adapted to allow for the amount of plasticiser used whilst maintaining their relative proportions.

The films of the invention are dry, i.e. are substantially, e.g. essentially, water-free (moisture-free). This may be expressed as a water content of less than 10% w/w, e.g. less than 9%, 8%, 7%, 6%, 5%, 4.5%, 4%, 3.5%, 3%, 2.5%, 2%, 1.5% or 1% w/w as measured by weight loss on drying or chemically by the Karl Fischer method (United States Pharmacopeia; European Pharmacopoeia). Any drying process employed in the preparation of the films of the invention will preferably not impart a 3D lattice structure or arrangement to the film.

In certain embodiments the films of the invention are bioadhesive, or more specifically, adhere to a wound. Preferably adherence is of sufficient permanency to last until the film disintegrates. This property may be achieved by selecting adhesive film forming materials, e.g. xanthan gum, tragacanth gum, guar gum, acacia gum, arabic gum, carrageenan and alginate, and/or adding a layer, boundary or area of adhesive to the film. In other approaches the film is designed to be hydrophilic as such a property would result in sufficient adhesion to a moist wound surface, e.g. by the action of the surface tension of the fluid at the wound surface. A "hydrophilic" film in the context of the films of the invention may be expressed as a film, or a portion thereof, which does not repel water molecules and, in some instances, attracts water molecules. A hydrophilic film may therefore be described as "wettable". In certain embodiments the hydrophilic (wettable) film may be "hygroscopic", i.e. will take up, take on or take in (absorb or adsorb) water molecules when provided in its dry form as defined herein. Hydrophilic films may therefore be considered to be a film, or portion thereof, capable of adsorbing and/or absorbing water in an amount equivalent to at least about 25%, e.g., at least about 30%, 35%, 40%, 45%, 50%, 55%, 60%, 65%, 70% or 75% of its mass when provided in a dry form as defined herein.

In a further embodiment the film of the invention is sufficiently pliable to allow the film, or a portion thereof, to be conformed to the target wound or target portion thereof. Alternatively or in addition the films of the invention will be sufficiently pliable to ensure the films remain substantially intact during transport, storage and use. Pliability of the films of the invention may be measured in terms of the Young's modulus of the film. Young's modulus can be calculated by dividing the tensile stress by the extensional strain in the elastic (initial, linear) portion of a stress-strain curve. Analysis of the stress-strain curves of a variety of films allows selection of a range of pliabilities which may be optimal for specific uses.

"Biocompatible" as used herein refers to the physiological, e.g. toxicological and/or immunological, tolerability of the film and its degradation products at its site of use and within the host organism. In other words, the ability to be in contact with a living system without producing an adverse effect. Particulate ESM and the films of the invention are predicted to be substantially, e.g. essentially, non-toxic and substantially, e.g. essentially, non-immunogenic and preferably substantially, e.g. essentially, non-irritant. Standard assays and acceptable thresholds for biocompatibility, and toxicity in particular, for body-contacting medical devices are provided in the International Standards Authority standard ISO10993 (Biological Evaluation of Medical Devices) and its collateral standards. The films of the invention are preferably essentially in compliance with ISO10993.

By "distributed uniformly" it is meant that the particulate ESM of the films of the invention is not accumulated to any significant degree in or on any part of the film. That is, any sample of a chosen size taken from the full thickness of a film of the invention will have essentially the same amount of particulate ESM (e.g. measured as % w/w) as a second sample of the same size from another part of the film. Expressed differently, a plurality of (e.g. 10) macroscopic full-thickness portions of a film (e.g. a portion with a volume of about 5 mm$^3$ or area of 5 mm$^2$) will on average (mean) contain (or carry) essentially the same proportion of particulate ESM as the entire film.

The film of the invention preferably comprises an amount of particulate ESM capable of eliciting a wound healing effect, e.g. as defined herein, when applied (administered) to a wound.

The term "film" is readily understood by persons skilled in the art. It may be used interchangeably herein with the terms "membrane", "sheet", "coating" and "layer", unless context dictates otherwise. In the context of the present invention and the field of wound dressings, film dressings are distinct from fibrous dressings in sheet form, e.g. sheet fabric, textile and paper dressings. Thus, films do not have a knitted, woven or felted structure formed from fibrous or filamentous (typically insoluble) materials.

In accordance with the invention the films have a depth (or height) dimension (or mean average thereof) that is negligible compared to the width and length dimensions. In certain embodiments the films of the invention have a height (or mean height) which is less than 5%, e.g. less than 1%, 0.5%, 0.1%, 0.05% or 0.01% of the width and/or length dimensions (or the mean thereof). In certain embodiments the films of the invention have a height (or mean height) of equal to or less than about 2.0 mm, e.g. equal to or less than about 1.9, 1.8, 1.7, 1.6, 1.5, 1.4, 1.3, 1.2, 1.1, 1.0, 0.95, 0.90, 0.85, 0.80, 0.75, 0.70, 0.65, 0.60, 0.55, 0.50, 0.45, 0.40, 0.35, 0.30, 0.25, 0.20, 0.15, 0.10, 0.09, 0.08, 0.07, 0.06, 0.05, 0.04, 0.03, 0.02 or 0.01 mm. Preferably the height of the film is substantially the same at all parts of the film. This may be contrasted with a "three dimensional" (3D) object, i.e. an object having a height/depth, width and length wherein no one of these dimensions is less than 5%, e.g. less than 10, 15, 20 or 25% of the largest dimension. A 3D object may be described as a space-filling (or void-filling or cavity-filling)

entity. Thus, a film is not a sponge, scaffold, foam or pad. In certain embodiments the films do not comprise pores or voids of dimensions which may enclose and retain a wound cell or inflammatory cell from a subject to which the film is administered.

In accordance with the invention the term "particulate ESM" may be a, or may be formed from at least one, particle of ESM having a mean particle diameter of up to 500 µm, e.g. up to 450, 400, 350, 300, 250, 200, 150, 125 or 100 µm. In certain embodiments particulate ESM may be a, or may be formed from at least one, particle of ESM having a mean particle diameter of less than 100 µm, e.g. less than 95, 90, 85, 80, 75, 70, 65, 60, 55, 50, 45, 40, 35, 30, 25, 20, 15, 10, 5, or 1 µm, e.g. less than 900, 850, 800, 750, 700, 650, 600, 550, 500, 450, 400, 350, 300, 250, 200, 150, 100, 50, 10, 5 or 1 nm.

In certain other embodiments particulate ESM may be a, or may be formed from at least one, particle of ESM having a mean particle diameter of equal to or greater than 1 nm, e.g. equal to or greater than 5, 10, 50, 100, 150, 200, 250, 300, 350, 400, 450, 500, 550, 600, 650, 700, 750, 800, 850, 900 or 950 nm, or equal to or greater than 1 µm, e.g. equal to or greater than 5, 10, 15, 20, 25, 30, 35, 40, 45, 50, 55, 60, 65, 70, 75, 80, 85, 90, 95, 100, 125, 150, 200, 250, 300, 350, 400, or 450 µm.

Any and all range endpoints derivable from the combination of any of these values are specifically contemplated.

ESM particles may be any shape. An ESM particle may be essentially symmetric or asymmetric. An ESM particle may be essentially spherical, prismatoidal or cylindrical. An ESM particle may be essentially irregular or regular or have regions of both. An ESM particle may be angular, rounded or tapered or have regions thereof. In certain embodiments an ESM particle may have one length dimension that is significantly greater than the others and so may be referred to as, for example, rod-shaped, needle-shaped or fibrous (rods, needles or fibres) and may be qualified as cylindrical or prismatoidal (e.g. cuboidal) depending on the cross-sectional shape substantial perpendicular to the dimension of significantly greater length.

In certain embodiments an ESM particle may have an aspect ratio between a first length dimension and a second length dimension arranged perpendicular thereto of at least 1.5 (first length dimension:second length dimension), e.g. at least 2, 3, 4, 5, 6, 7, 8, 9, 10, 12, 14, 16, 18, 20, 25, 30, 35, 40, 45, 50, 55, 60, 65, 70, 80, 90 or 100. In other embodiments an ESM particle may have an aspect ratio between a first length dimension and a second length dimension arranged substantially perpendicular thereto of no greater than 2 (first length dimension:second length dimension), e.g. no greater than 3, 4, 5, 6, 7, 8, 9, 10, 12, 14, 16, 18, 20, 25, 30, 35, 40, 45, 50, 55, 60, 65, 70, 80, 90 or 100. Any and all range endpoints derivable from the combination of any of these values are specifically contemplated, e.g. an ESM particle may have an aspect ratio of any of 5, 6, 7, 8, 9 or 10 to any of 20, 25, 30, 35, 40, 45, 50, 55, 60, 65 or 70.

In these embodiments the first length dimension is the longest length dimension in the particle and may be termed the longitudinal dimension. The second length dimension may therefore be termed a lateral dimension. The second length dimension is the longest lateral dimension or a mean average value of the lateral dimensions of the particle.

In certain embodiments the longitudinal dimension is 0.1 µm to 500 µm, e.g. 0.1 µm to 400 µm, 0.1 µm to 300 µm, 0.1 µm to 200 µm, 0.1 µm to 100 µm, 0.1 µm to 80 µm, 0.1 µm to 60 µm, 0.1 µm to 40 µm, 0.1 µm to 20 µm, 0.1 µm to 10 µm, 0.1 µm to 1 µm, 0.1 µm to 0.5 µm, 0.5 µm to 500 µm, 0.5 µm to 400 µm, 0.5 µm to 300 µm, 0.5 µm to 200 µm, 0.5 µm to 100 µm, 0.5 µm to 80 µm, 0.5 µm to 60 µm, 0.5 µm to 40 µm, 0.5 µm to 20 µm, 0.5 µm to 10 µm, 0.5 µm to 1 µm, 1 µm to 500 µm, 1 µm to 400 µm, 1 µm to 300 µm, 1 µm to 200 µm, 1 µm to 100 µm, 1 µm to 80 µm, 1 µm to 60 µm, 1 µm to 40 µm, 1 µm to 20 µm, 1 µm to 10 µm, 10 µm to 500 µm, 10 µm to 400 µm, 10 µm to 300 µm, 10 µm to 200 µm, 10 µm to 100 µm, 10 µm to 80 µm, 10 µm to 60 µm, 10 µm to 40 µm, 10 µm to 20 µm, 20 µm to 500 µm, 20 µm to 400 µm, 20 µm to 300 µm, 20 µm to 200 µm, 20 µm to 100 µm, 20 µm to 80 µm, 20 µm to 60 µm, 20 µm to 40 µm, 40 µm to 500 µm, 40 µm to 400 µm, 40 µm to 300 µm, 40 µm to 200 µm, 40 µm to 100 µm, 40 µm to 80 µm, 40 µm to 60 µm, 60 µm to 500 µm, 60 µm to 400 µm, 60 µm to 300 µm, 60 µm to 200 µm, 60 µm to 100 µm, 60 µm to 80 µm, 80 µm to 500 µm, 80 µm to 400 µm, 80 µm to 300 µm, 80 µm to 200 µm, 80 µm to 100 µm, 100 µm to 500 µm, 100 µm to 400 µm, 100 µm to 300 µm, 100 µm to 200 µm, 200 µm to 500 µm, 200 µm to 400 µm, 200 µm to 300 µm, 300 µm to 500 µm, 300 µm to 400 µm or 400 µm to 500 µm.

In certain embodiments the lateral dimension, or average thereof, is 0.01 µm to 20 µm, e.g. 0.01 µm to 16 µm, 0.01 µm to 12 µm, 0.01 µm to 8 µm, 0.01 µm to 4 µm, 0.01 µm to 2 µm, 0.01 µm to 1.6 µm, 0.01 µm to 1.2 µm, 0.01 µm to 0.8 µm, 0.01 µm to 0.4 µm, 0.01 µm to 0.2 µm, 0.01 µm to 0.1 µm, 0.01 µm to 0.05 µm, 0.05 µm to 20 µm, 0.05 µm to 16 µm, 0.05 µm to 12 µm, 0.05 µm to 8 µm, 0.05 µm to 4 µm, 0.05 µm to 2 µm, 0.05 µm to 1.6 µm, 0.05 µm to 1.2 µm, 0.05 µm to 0.8 µm, 0.05 µm to 0.4 µm, 0.05 µm to 0.2 µm, 0.05 µm to 0.1 µm, 0.1 µm to 20 µm, 0.1 µm to 16 µm, 0.1 µm to 12 µm, 0.1 µm to 8 µm, 0.1 µm to 4 µm, 0.1 µm to 2 µm, 0.1 µm to 1.6 µm, 0.1 µm to 1.2 µm, 0.1 µm to 0.8 µm, 0.1 µm to 0.4 µm, 0.1 µm to 0.2 µm, 0.2 µm to 20 µm, 0.2 µm to 16 µm, 0.2 µm to 12 µm, 0.2 µm to 8 µm, 0.2 µm to 4 µm, 0.2 µm to 2 µm, 0.2 µm to 1.6 µm, 0.2 µm to 1.2 µm, 0.2 µm to 0.8 µm, 0.2 µm to 0.4 µm, 0.4 µm to 20 µm, 0.4 µm to 16 µm, 0.4 µm to 12 µm, 0.4 µm to 8 µm, 0.4 µm to 4 µm, 0.4 µm to 2 µm, 0.4 µm to 1.6 µm, 0.4 µm to 1.2 µm, 0.4 µm to 0.8 µm, 0.8 µm to 20 µm, 0.8 µm to 16 µm, 0.8 µm to 12 µm, 0.8 µm to 8 µm, 0.8 µm to 4 µm, 0.8 µm to 2 µm, 0.8 µm to 1.6 µm, 0.8 µm to 1.2 µm, 1.2 µm to 20 µm, 1.2 µm to 16 µm, 1.2 µm to 12 µm, 1.2 µm to 8 µm, 1.2 µm to 4 µm, 1.2 µm to 2 µm, 1.2 µm to 1.6 µm, 1.6 µm to 20 µm, 1.6 µm to 16 µm, 1.6 µm to 12 µm, 1.6 µm to 8 µm, 1.6 µm to 4 µm, 1.6 µm to 2 µm, 2 µm to 20 µm, 2 µm to 16 µm, 2 µm to 12 µm, 2 µm to 8 µm, 2 µm to 4 µm, 4 µm to 20 µm, 4 µm to 16 µm, 4 µm to 12 µm or 4 µm to 8 µm.

Any and all combinations of longitudinal and lateral dimensions, and ranges thereof, disclosed above are specifically contemplated, in particular in combination with any and all aspect ratios, and ranges thereof. In view of the foregoing it may be seen that certain ESM particles of use in the invention are rods, needles or fibres. In accordance with the above, in embodiments in which rod, needle or fibre forms of particulate ESM are used, the resultant film does not have a knitted, woven or felted structure on account of the sizes of particles used and/or the amounts of particles present in the film.

In view of the generality of the invention with regard to ESM particle shape, in the context of ESM particles which are not substantially, e.g. essentially, spherical, references to ESM particle diameters are therefore references to equivalent spherical diameter. In these embodiments the ESM particle has a shape defined by size dimensions that would result in the same size readings as a sphere of the same substance composition of said diameter in the particle size measuring technique used. In certain embodiments the size dimensions used are volume or surface area, preferably volume.

The mean (average) diameter, or equivalent spherical diameter, may be assessed by any convenient means, e.g. resistive pulse/Coulter method, sedimentation (gravity or centrifugation), optical imaging (e.g. SEM, static image analysis, dynamic image analysis), laser diffraction or light scattering, but for the purposes of the invention the Coulter method, in the form of Tunable Resistive Pulse Sensing, or optical means should be used to determine particle size.

It is believed that ESM particles with a high aspect ratio, e.g. fibres, rods or needles, and of the above described sizes (which may be interchangeably referred to herein as micro-fibres, micro-rods and micro-needles or nano-fibres, nano-rods and nano-needles depending on size) will have certain physical advantages over other forms of ESM (e.g. those of WO 2004/080428) at least in the context of wound healing treatments described herein. In particular, such arrangements are believed to be able to provide ideal levels of surface area, turnover rates, wettability, moisture retention, spreadability and, in particular, MMP inhibition.

In certain embodiments the particle of use in the invention is not substantially, e.g. essentially, spherical, i.e. is not a particle with an aspect ratio as defined above of less than 1.5, e.g. 1.4, 1.3, 1.2 or 1.1. In other embodiments the particle of use in the invention is not a sphere, i.e. is not a particle with an aspect ratio as defined above of 1.

The particulate ESM defined above will typically be a plurality of said ESM particles, said plurality of particles having a mode particle diameter up to 500 μm, e.g. up to 450, 400, 350, 300, 250, 200, 150, 125 or 100 μm. In certain embodiments the plurality of particles has a mode particle diameter of less than 100 μm, e.g. less than 95, 90, 85, 80, 75, 70, 65, 60, 55, 50, 45, 40, 35, 30, 25, 20, 15, 10, 5, or 1 μm, e.g. less than 900, 850, 800, 750, 700, 650, 600, 550, 500, 450, 400, 350, 300, 250, 200, 150, 100, 50, 10, 5 or 1 nm.

In certain embodiments the plurality of particles also has a mode particle diameter of equal to or greater than 1 nm, e.g. equal to or greater than 5, 10, 50, 100, 150, 200, 250, 300, 350, 400, 450, 500, 550, 600, 650, 700, 750, 800, 850, 900 or 950 nm, or equal to or greater than 1 μm, e.g. equal to or greater than 5, 10, 15, 20, 25, 30, 35, 40, 45, 50, 55, 60, 65, 70, 75, 80, 85, 90, 95, 100, 125, 150, 200, 250, 300, 350, 400, or 450 μm. Any and all range endpoints derivable from the combination of any of these values are specifically contemplated.

In certain embodiments less than 25%, e.g. less than 20%, 15%, 10%, 9%, 8%, 7%, 6%, 5%, 4%, 3%, 2%, 1%, 0.5% or 0.1% of the number of particles within said plurality of particles have a mean particle diameter equal to or greater than 500, e.g. equal or greater than 450, 400, 350, 300, 250, 200, 150, 125, 100, 95, 90, 85, 80, 75, 70, 65, 60, 55, 50, 45, 40, 35, 30, 25, 20, 15, 10, 5, or 1 μm, e.g. equal to or greater than 900, 850, 800, 750, 700, 650, 600, 550, 500, 450, 400, 350, 300, 250, 200, 150, 100, 50, 10, 5 or 1 nm. In certain embodiments it may be advantageous to use a plurality of ESM particles with low dispersity. In other embodiments the plurality of ESM particles are essentially monodisperse. On the other hand, in certain other embodiments a broad range of ESM particle sizes or a plurality of more narrow particle size ranges may be selected to achieve one or more of the various physiological effects described herein. Without wishing to be bound by theory, ESM particles of use in the invention having a mean particle diameter at the upper end of the size range may facilitate wound cell migration by providing a greater scaffolding effect whereas ESM particles of use in the invention having a mean particle diameter at the bottom end of the size range may have a greater inhibitory effect on MMPs and inflammation. It may be advantageous to select different size ranges in order to tailor the physiological effects of the ESM particles of use in the invention.

ESM is the fibrous bilayer found in an egg between the albumen and the eggshell of avian eggs, e.g. the eggs of fowl (gamefowl/landfowl (Galliformes) and waterfowl (Anseriformes)) and poultry, in particular chicken, duck, goose, turkey, guineafowl, ostrich, pigeon, pheasant, partridge, grouse or gull. The eggs of *Gallus gallus domesticus*, the domestic chicken, are especially preferred. Either or both layers of the bilayer may be used in accordance with the invention.

Preferably the particulate ESM and the film as a whole is essentially free of other (non-ESM) egg components (which may be considered "contaminating" substances vis a vis ESM), e.g. albumen, yolk, and/or egg shell (calcium carbonate). By "essentially free" it is meant that the particulate ESM (and ESM particles they comprise) of use in accordance with the invention, and in other embodiments the films of the invention contain no more than 5% w/w, e.g. no more than 4%, 3%, 2%, 1%, 0.5%, 0.1%, 0.05% or 0.01% w/w of non-ESM egg components.

The ESM of the particulate ESM of the invention may be separated from other egg components by any convenient means. The eggs from which the ESM may be separated may be fertilised or unfertilised. The eggs may be intact, i.e. prior to hatching, or may be empty, i.e. the remnants of the egg following hatching or following extraction of the egg contents (albumen and yolk). Suitable means are for example described in WO 2004/080428 and U.S. Pat. No. 8,580,315, the contents of which are incorporated herein by reference. Preferably the ESM is prepared by the method for harvesting eggshell membrane in-line in commercial egg processing plants disclosed in WO 2015/058790 the contents of which are incorporated herein by reference. In brief WO 2015/058790 provides a method of processing eggshell residues, which emanate from an egg breaking unit and comprise eggshell portions as well as membrane portions, comprising feeding eggshell residues (e.g. having a particle size of about 0.5 mm to about 40 mm and a wet basis moisture content of about 3% to about 40%) from the egg breaking unit into a cyclone driven by a process gas having a temperature of less than about 85° C. (preferably of less than about 60° C.) and having a speed exceeding about 60 m/s (preferably between about 70 m/s and about 340 m/s). Within said cyclone vortex processing of the eggshell residues reduces particle size and peels said membrane portions off of said eggshell portions, such that said eggshell portions become separated from said membrane portions. Through a top outlet of said cyclone there is released mainly a mix of process gas, vapour and droplets, and through a bottom outlet of said cyclone there is released mainly a mixture of separated eggshell portions and membrane portions. Said released mixture is then separated into an eggshell portion part and a membrane portion part in a sorting device. The resultant ESM portion may then be processed further into the ESM particles of the invention as described herein, preferably with no intervening steps.

In certain embodiments the method of preparing ESM comprises the further step of controlling time between feeding eggshell residues into and releasing said mixture out of said cyclone by adjusting an eggshell residue feed rate in relation to a total process gas feed rate, e.g. into an interval of about 0.5 s to about 20 s and preferably of about 1 s to about 5 s. In certain embodiments the method further comprises a step of centrifuging the eggshell residues prior to feeding them into said cyclone. In certain embodiments the feeding step is continuous. In other embodiments the sorting step comprises pneumatically expelling the membrane portion part off of sorting screens and out of the sorting device. The method may also comprise a final step of drying the membrane portion part.

ESM material in the form of flakes within the size range of around 1 mm$^2$ to about 10 mm$^2$ cannot be re-formed or processed into a sheet with the same structural characteristics as intact ESM.

In certain embodiments the particulate ESM of use in the invention (or at least the protein components thereof) will be substantially that obtained from the shell-membrane separation process. In other words, the particulate ESM of use in the invention will be substantially chemically unmodified as compared to naturally occurring ESM from a corresponding avian source.

More specifically the particulate ESM of use in the invention will be chemically substantially non-degraded, non-digested (e.g. chemically or enzymatically) and/or non-denatured as compared to naturally occurring ESM from a corresponding avian source. By "substantially non-degraded" it is meant that less than 20%, e.g. less than 15%, 10%, 5% or 1% of the ESM components will show evidence of degradation as compared to naturally occurring ESM from a corresponding avian source. Non-digested and non-denatured should be interpreted accordingly. The degree of degradation/digestion/denaturation of ESM can be assessed by measuring the relative solubility of the ESM and/or the relative size or structure of the collagen fibres in the ESM. This may be achieved through routine techniques including immunohistochemistry/immunocytochemistry techniques and/or biomolecule (e.g. protein) stains and dyes.

In particular in certain embodiments the particulate ESM of use in the invention will not have been exposed to a hydrolysis reaction or a disulphide bond reducing reaction, e.g. chemical or enzymatic, in particular an alkaline hydrolysis reaction. In other words the particulate ESM of use in the invention will be substantially non-hydrolysed, by which it is meant that less than 20%, e.g. less than 15%, 10%, 5% or 1% of the ESM components will show evidence of hydrolysis as compared to naturally occurring ESM from a corresponding avian source. The degree of hydrolysis of ESM can be assessed by measuring the relative solubility of the ESM and/or the relative size of the collagen fibres and/or the extent of collagen cross-linking in the ESM. This may be achieved through routine techniques including immunohistochemistry/immunocytochemistry techniques and/or protein stains and dyes.

In other embodiments the particulate ESM of use in the invention will be substantially, e.g. essentially, insoluble in water at a neutral pH, e.g. pH 6.8-7.2. For the purposes of the invention an insoluble material requires greater than 10 L of solvent to dissolve 1 g of solute.

The particulate ESM of use in the invention may be prepared from ESM by any convenient particle size reduction, micronizing, grinding, pulverizing or milling technology means, e.g. ball milling, bead milling, jet milling, vortex milling, blade milling, rotor-stator dispersement, preferably followed by size selection, e.g. sieving and screening. The chosen particle size reduction method may be either performed dry or with a liquid medium which may or may not comprise other components of the film. Cryo-pulverization may also be employed. In certain embodiments the particle size reduction process, and in certain embodiments the preceding ESM preparation process, is selected on the basis that ESM fibres of the required size (e.g. as recited above) are produced. Inter alia, pulverisation of dry ESM in a blade-mill and rotor-stator dispersement of a suspension of ESM flakes have been shown to be effective in this regard.

Thus, in accordance with the invention, a method for the preparation of particulate ESM of use in the invention may comprise providing ESM, e.g. as defined herein, and subjecting the ESM to a micronization process. Preferably the ESM is provided essentially free of non-ESM egg components and more preferably providing ESM essentially free of non-ESM egg components comprises separating ESM from non-ESM egg components, e.g. as described in WO 2015/058790, and above and washing the ESM so obtained with a weak acid solution (which term includes a weakly acidic solution), e.g. an aqueous solution of 0.1% hydrochloric acid or acetic acid, thereby removing any residual calcium carbonate in the ESM. In other embodiments the micronized ESM is washed with said weak acid solution. This weak acid wash, especially treatment with an about 0.1% HCl solution, not only demineralises the ESM, thus minimising the amount of inorganic salts in the ESM, but also removes and/or inactivates infective agents, e.g. microorganisms (e.g. as described herein), prions and viruses. Micronization of ESM prepared in this way produces ESM fibres of 10-100 μm in length and a thickness of 1-5 μm (i.e. micro-fibres and nano-fibres). Additional components of the film of the invention may be included prior to the micronization process, during said process or after said process.

The films of the invention may comprise excipients insofar as the above recited proportions of film forming material and particulate ESM allows. Such excipients are biocompatible, non-toxic and preferably non-irritating. The excipients may additionally include lubricating agents, wetting agents, emulsifying agents, suspending agents, preserving agents, buffering agents, humectants, plasticisers and the like. Examples of suitable excipients are lactose, dextrose, sucrose, sorbitol, mannitol, glycerol, urea, calcium phosphate, calcium silicate, methylhydroxybenzoates, propyl hydroxybenzoates, talc, magnesium stearate, mineral oil or fatty substances such as hard fat or suitable mixtures thereof. In certain embodiments the excipient will not be sheet or flaked ESM, or indeed solid ESM in any form, or prepared from ESM derived materials or components (e.g. ESM hydrolysates or proteins and/or polysaccharides isolated from ESM). For the purposes of the present invention the excipient will not be a film forming material and vice versa.

The films of the invention may also comprise further therapeutically active agents in addition to the particulate ESM and the film forming material insofar as the above recited proportions of film forming material and particulate ESM and optionally further excipients allows. For the purposes of the present invention the further therapeutically active agents will not be a film forming material, although it may be that a film forming material has a therapeutic effect in the context of the use films of the invention. Thus, a further therapeutically active agent may be described as a therapeutic agent which does not perform an essential structural role in the film.

Suitable further therapeutically active agents which may be incorporated into the films of the invention may include, but not be limited to, clinically-useful anti-microbial agents (e.g. antibiotics, antiseptics, antimicrobial surfactants, anti-fungals, antivirals), a growth factor, or an anti-inflammatory agent (which may be referred to as a "further anti-microbial agent", "further growth factor" or "further anti-inflammatory agent" if the ESM particles used already have such properties). Such agents may be present in the films in amounts of less than 25% w/w, e.g. less than 20%, 15%, 10%, 5% or 1% w/w.

Representative antibiotics include, but are not limited to the aminoglycosides (e.g. amikacin, gentamicin, kanamycin, neomycin, netilmicin, streptomycin, tobramycin); the carbecephems (e.g. loracarbef); the 1st generation cephalosporins (eg cefadroxil, cefazolin, cephalexin); 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the macrolides (e.g. azithromycin, clarithromycin, dirithromycin, erythromycin, troleandomycin); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin); the polypeptide antibiotics (e.g. bacitracin, colistin, polymyxin B); the quinolones (e.g. ciprofloxacin, enoxacin, gatifloxacin, levofloxacin, lomefloxacin, moxifloxacin, norfloxacin, ofloxacin, trovafloxacin); the sulfonamides (e.g. mafenide, sulfacetamide, sulfamethizole, sulfasalazine, sulfisoxazole, trimethoprim-sulfamethoxazole); the tetracyclines (e.g. demeclocycline, doxycycline, minocycline, oxytetracycline, tetracycline); the carbapenems (e.g. imipenem, meropenem, ertapenem, doripenem, panipenem/betamipron, biapenem, PZ-601); chloramphenicol; clindamycin, ethambutol; fosfomycin; isoniazid; linezolid; metronidazole; nitrofurantoin; pyrazinamide; quinupristin/dalfopristin; rifampin; spectinomycin; and vancomycin.

Representative antiseptics include, but are not limited to chlorine bleach (sodium hypochlorite), quaternary ammonium compounds (e.g. benzalkonium chloride, cetyl trimethylammonium bromide, cetylpyridinium chloride), hydrogen peroxide, phenol compounds (e.g. TCP Triclosan), alcohols (e.g. ethanol), Virkon™ iodine compounds (e.g. povidone-iodine), silver, copper, iron, lead, zinc, bismuth, gold and aluminium compounds (e.g. elemental silver, copper, iron, lead, zinc, bismuth, gold and aluminium nano/microparticles).

Antimicrobial surfactants are another class of antiseptics. These are compounds that disrupt microbial cell membranes and other structural components and therefore inhibit growth and/or viability of microorganisms. Antimicrobial surfactants and their use in antimicrobial compositions is well known in the art should further guidance be needed the discussion of antimicrobial surfactants in "Preservative-free and self-preserving cosmetics and drugs—Principles and practice", Ed. Kabara and Orth, Marcel Dekker, N.Y., N.Y., 1997, is explicitly incorporated by reference in its entirety. Antimicrobial surfactants may be anionic, cationic, non-ionic or amphoteric. Examples of antimicrobial anionic surfactants include, but are not limited to, sodium dodecyl sulfate (sodium lauryl sulfate), sodium dodecyl aminopropionic acid, sodium ricinoleate, bile acids, alkylaryl sulfonates, Grillosan DS7911, disodium undecylenic acid monoethanol amidosulfosuccinate. Examples of antimicrobial cationic surfactants include, but are not limited to, the quaternary ammionium compounds, the aminimides and chlorhexidine compounds. Examples of antimicrobial non-ionic surfactants include, but are not limited to, the monoesters of fatty acids, polyethyleneglycomonoesters of alkyldihydroxybenzoic acids, glucosamine derivatives and diethanolamides of N-lauroyl dipeptides. Examples of antimicrobial amphoteric surfactants include, but are not limited to, the alkyl betaines, the alkylamidopropylbetaines, the alkyl aminopropionates, the alkyliminodipropionates and the alkylimidazolines.

Representative antifungals include, but are not limited to the polyenes (e.g. natamycin, rimocidin, filipin, nystatin, amphotericin B, candicin; the imidazoles (e.g. miconazole, ketoconazole, clotrimazole, econazole, bifonazole, butoconazole, fenticonazole, isoconazole, oxiconazole, sertaconazole, sulconazole, tioconazole); the triazoles (e.g. fluconazole, itraconazole, isavuconazole, ravuconazole, posaconazole, voriconazole, terconazole); the allylamines (e.g. terbinafine, amorolfine, naftifine, butenafine); and the echinocandins (e.g. anidulafungin, caspofungin, micafungin).

Representative antivirals include, but are not limited to abacavir, acyclovir, adefovir, amantadine, amprenavir, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type, II interferon type I, lamivudine, lopinavir, loviride, maraviroc, moroxydine, nelfinavir, nevirapine, nexavir, oseltamivir, penciclovir, peramivir, pleconaril, podophyllotoxin, raltegravir, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

Representative growth factors include, but are not limited to, platelet-derived growth factor (PDGF), basic and acidic fibroblast growth factor (FGF), epidermal growth factor (EGF), hepatocyte growth factor (hGF), growth hormone (GH), bone morphogenic proteins 2 and 7 (BMP2 and BMP7), insulin-like growth factors I and II (IGF-I, IGF-II), transforming growth factor (TGF-β1, TGF-β2), keratinocyte growth factor (KGF), migration-stimulating factor (MSF), vascular endothelial growth factor (VEGF), nerve growth factor (NGF) and brain-derived neurotrophic factor (BDNF).

Representative anti-inflammatory agents include, but are not limited to an anti-inflammatory steroid (e.g. a corticosteroid), an NSAID or an anti-inflammatory cytokine. Representative NSAIDs include, but are not limited to, the salicylates (e.g. aspirin (acetylsalicylic acid), choline magnesium trisalicylate, diflunisal, salsalate, the propionic acid derivatives (e.g. ibuprofen, dexibuprofen, dexketoprofen, fenoprofen, flurbiprofen, ketoprofen, loxoprofen naproxen, oxaprozin), the acetic acid derivatives (e.g. aceclofenac, diclofenac, etodolac, indomethacin, ketorolac, nabumetone, tolmetin, sulindac), the enolic acid derivatives (e.g. droxicam, isoxicam, lornoxicam, meloxicam, piroxicam, tenoxicam), the anthranilic acid derivatives (e.g. flufenamic acid, meclofenamic acid, mefenamic acid, tolfenamic acid) and the selective COX-2 inhibitors (Coxibs; e.g. celecoxib, etoricoxib, lumiracoxib, parecoxib, rofecoxib, valdecoxib). The propionic acid derivatives (e.g. ibuprofen, dexibuprofen, dexketoprofen, fenoprofen, flurbiprofen, ketoprofen, loxoprofen naproxen, oxaprozin) are preferred, ibuprofen being most preferred. Representative anti-inflammatory cytokines include (IL)-1 receptor antagonist, IL-4, IL-6, IL-10, IL-11, and IL-13.

The films of the invention may also be provided as coloured films, e.g. to facilitate their placement in or on the wound. In such embodiments the films of the invention can also contain (further) specific colouring agents or colorants insofar as the above recited proportions of film forming material and particulate ESM and optionally further active agent and/or excipient allows. For the purposes of the present invention the colouring agents or colorants referred to in these embodiments will not be a film forming material, although it may be that a film forming material has a colorant effect in the context of the use films of the invention. Thus, a colouring agent or colorant as referred to in these embodiments does not perform an essential structural role in the film.

The colouring agents are used in amounts effective to produce the desired colour. The colouring agents useful in the present invention include pigments such as titanium dioxide, which may be incorporated in amounts of up to about 5% w/w, and preferably less than about 1%. Colorants can also include natural food colours and dyes suitable for food, drug and cosmetic applications. The materials acceptable for the foregoing spectrum of use are preferably water-soluble, and include FD & C Blue No. 2, which is the disodium salt of 5,5 indigotindisulfonic acid. Similarly, the dye known as Green No. 3 comprises a triphenylmethane dye and is the monosodium salt of 4-[4-N-ethyl-p-sulfobenzylamino) diphenyl-methylene]-[I—N-ethyl-N-p-sulfonium benzyl)2,5-cyclo-hexadienimine]. A full recitation of all FD & C and D & C dyes and their corresponding chemical structures may be found in the Kirk-Othmer Encyclopedia of Chemical Technology, Volume 5, Pages 857-884, which text is accordingly incorporated herein by reference.

The films of the invention are preferably capable of being terminally sterilised e.g. by an ionizing source (for instance gamma radiation) or by a chemical gaseous source (for instance ethylene oxide). The films of the invention may therefore comprise stabilising excipient agents to provide resistance to induced chemical and physical changes due to the cross-linking effect created during treatment with ionizing radiation. Specifically, the films may include excipient materials which act as free-radical scavengers and antioxidants.

The films of the invention may be provided and used as they are or as a part of a multilayer film comprising one or more of the films of the invention. In other instances the films of the invention may be incorporated into or used together with a further wound dressing e.g. a woven and/or non-woven dry fibrous (e.g. fabric, textile or paper) dressing, a non-disintegratable (e.g. plastic) film dressing, a gel-based dressing or a dressing which is a combination of these dressing types. The composite dressings will typically be adapted or used such that the films of the invention will be exposed to the wound or wound exudate when in use. In still further embodiments the films of the present invention may be applied to the further dressing prior to or during its application to a wound. Alternatively the films may be applied to the wound, including one or more repositionings if necessary, prior to application of the further wound dressing.

Fibrous dressings typically have a knitted, woven or felted structure formed from fibrous or filamentous (typically insoluble) materials. Fibrous dressings of use in these embodiments of the invention may include dressings formed from fibres or filaments of cotton, alginate, insoluble cellulose (e.g. oxidised regenerated cellulose, carboxymethylcellulose, hydroxyethylcellulose), fibrous collagen, and ESM (U.S. Pat. No. 7,767,297, incorporated herein by reference). Fibrous dressings therefore include sheet fabric, textile and paper dressings.

Non-disintegratable film dressings are typically semi- or impermeable to water and flexible and may be formed from any suitable plastic, e.g. polyurethane, polyvinylchloride.

Gel-based dressings, which include hydrogels and hydrocolloid gels, may be formed from a plethora of polymeric substances, including, but limited to, alginate, cellulose (e.g. oxidised regenerated cellulose, methylcellulose, carboxymethylcellulose, hydroxyethylcellulose), collagen, pectin, elastin, fibronectin. The inclusion of biopolymers, gums or resins (e.g. gelatin) can help ensure that the dressing adheres lightly to the wound surface. The inclusion of alginate may increase the moisture capacity of the gel matrix. Such basic alginate gels for wound healing are described in U.S. Pat. No. 6,201,164. Should the gel based dressing selected for use with the film be a moist or liquid dressing, contact between the film of the invention and the second dressing will usually take place once the film is contacted with the target wound, or essentially immediately prior to the composite dressing being applied to the wound to avoid premature disintegration.

The films of the invention may be prepared by any convenient means, e.g. any convenient casting, drawing, or extruding technique. For example, a solution or dispersion of film forming material, and optionally particulate ESM, may be sprayed onto a support, e.g. a plastic sheet or a release-treated belt. Alternatively, for example, the solution or dispersion of film forming material may be roll coated onto a release treated paper or film substrate. After coating of the solution or dispersion onto a support surface, the solvent may be removed by radiant energy (such as infrared), heat, convection, vacuum, or any combination of these to yield a dry film. The resulting dry film can be wound up into a roll for storage prior to further processing into unit dose forms. Whether stored for future processing or immediately following preparation, the resulting film can be removed from the support surface and subsequently processed into unit dose form. Additional ingredients, e.g. the particulate ESM, can be applied to the dried film by, for example, printing, spraying, dusting, or vapour adsorption processes, among others.

The principal large scale manufacturing methods for thin disintegratable films are described Misha and Amin (2011, Pharmaceutical Technology 35,1). Disintegratable films are most conveniently manufactured using the solvent-casting method. First, the water-soluble ingredients of the film are dissolved to form a viscous solution. This mixture may include plasticizers and other materials to optimize the mechanical and solubility properties of the film. This solution is cast as a film of a specified thickness and allowed to dry. The thickness of solution applied to the surface defines the thickness of the final dried film. In industrial scale processes, the casting and drying are done in a continuous roll system known as knife-over-roll coating system.

To achieve uniform distribution of the particulate ESM within the films of the invention it may be advantageous to combine the particulate ESM with the other film components prior to formation of the film, e.g. as described above.

In a specific embodiment there is therefore provided a method for preparing a film of the invention as defined herein, said method comprising (i) providing particulate ESM and said film forming material in a liquid suspension, and (ii) drying the suspension, optionally in a mould or on a flat surface, thereby obtaining said film.

In certain embodiments step (i) of providing particulate ESM and said film forming material in a liquid suspension (preferably an aqueous suspension) comprises providing ESM in the form of a sheet or flakes and said film forming material in an aqueous suspension and applying an ESM size reduction technique, e.g. those described herein, to said suspension. The use of a rotor-stator disperser may be advantageous.

In other embodiments step (i) of providing particulate ESM and said film forming material in a liquid suspension comprises providing particulate ESM and said film forming material and combining one or other or both with a liquid to form said suspension. This may involve combining one or more of the film forming materials with a liquid suspension of said particulate ESM, or combining said particulate ESM with a solution or a liquid suspension of one or more of the film forming materials, or combining a liquid suspension of said particulate ESM with a solution or a liquid suspension of said film forming material. Further size reduction of the ESM may take place at any point. In these embodiments the liquid suspension is preferably an aqueous suspension.

In these aspects the film forming materials may be any of those disclosed herein and the accompanying discussion of preferred features and the like, especially amounts and relative proportions, applies mutatis mutandis to these aspects.

In certain embodiments the film forming material will comprise, e.g. consist essentially of, or consist of, collagen and/or gelatin, preferably collagen. In these embodiments the weight ratio of particulate ESM to the collagen and/or gelatin component will be 1:10 to 10:1, e.g. 1:10 to 1:1, 1:6 to 1:1, 1:3 to 1:1, or about 1:1. Further suitable ratios are described herein.

In certain embodiments the film forming material will comprise, e.g. consist essentially of, or consist of, hydroxyethylcellulose. In these embodiments the weight ratio of particulate ESM to the hydroxyethylcellulose component will be 1:19 to 19:1, e.g. 1:10 to 1:1, 1:6 to 1:1, 1:4 to 1:1, 1:3 to 1:1, 1:2 to 1:1 or about 1:1. Further suitable ratios are described herein.

In certain embodiments the film forming material will comprise, e.g. consist essentially of, or consist of, carboxymethylcellulose. In these embodiments the weight ratio of particulate ESM to the carboxymethylcellulose component will be 1:19 to 19:1, e.g. 1:10 to 1:1, 1:6 to 1:1, 1:4 to 1:1, 1:3 to 1:1, 1:2 to 1:1 or about 1:1. Further suitable ratios are described herein.

In certain embodiments the film forming material will comprise, e.g. consist essentially of, or consist of, hydroxypropylcellulose. In these embodiments the weight ratio of particulate ESM to the hydroxypropylcellulose component will be 1:19 to 19:1, e.g. 1:10 to 1:1, 1:6 to 1:1, 1:4 to 1:1, 1:3 to 1:1, 1:2 to 1:1 or about 1:1. Further suitable ratios are described herein.

Various sizes of the cellulose compound may be used together within the above recited proportions in order to adjust the properties, e.g. the disintegration rate, of the film. A plasticiser may also be incorporated into these cellulose derivative based films.

In certain embodiments the method includes a step in which the ESM of the particulate ESM provided in step (i) has been or is contacted with an acid at a concentration and for a time sufficient to hydrate the ESM (and preferably solubilise any collagen and/or gelatin present in mixture with the ESM), e.g. acetic acid at a concentration of about 0.5M (e.g. 0.1 to 1M, 0.3 to 0.7M or 0.4 to 0.6M). Alternative acids may be used but the choice of acid may influence the characteristics of the films. Acetic acid is preferred for the optimal the preparation of the films of the invention.

In a further specific embodiment there is also provided a method for preparing a film of the invention as defined herein, said method comprising
(i) providing a dry biocompatible film formed from at least one film forming material, wherein said film, or portion thereof, disintegrates upon contact with a wound or an exudate thereof, and
(ii) applying particulate ESM uniformly to at least one surface of the film.

In these embodiments the particulate ESM may be applied to the film by any means which may result in uniform distribution on the film surface but not significant disintegration of the film and retention of the particulate ESM by the film or film surface, e.g. by printing, spraying, dusting, or vapour adsorption processes, among others. Embodiments will therefore depend on the disintegration trigger of the film in question. If the film is water soluble, application options may include the application of particulate ESM in a non-aqueous suspension, or the use of an non water-based adhesive on the particles and/or the surface to be treated. If for instance degradation of the film is mediated by an enzyme and not moisture, an aqueous suspension of particulate ESM could be used.

A particulate ESM containing film (i.e. a dry biocompatible film comprising at least one film forming material and particulate ESM, wherein said particulate ESM is distributed substantially uniformly in and/or on the film and wherein said film, or portion thereof, disintegrates upon contact with a wound or an exudate thereof) obtained or obtainable by said methods of the invention is a further aspect of the invention.

The particulate ESM containing films of the invention can also be applied to the surfaces of implantable medical devices and thus application to a wound may be achieved in this way also. Such medical devices may be those described herein including but not limited to, any kind of percutaneous devices and/or line which results in a wound (e.g. central venous catheters, in particular catheters with cuffs, e.g. Dacron or collagen cuffs), prosthetic devices, e.g., heart valves, artificial joints, dental implants and artificial soft tissue implants (e.g. breast, buttock and lip implants), stents, pacemakers, and tracheostomy tubes.

The clinical usefulness of catheters, for example haemodialysis catheters, is limited where these become infected (Wayne et al 2005; J Am Soc Nephrol 16: 1453-1462). Exit sites may be treated with antibiotics to reduce bacterial growth but such use is often associated with the development of antibiotic resistance. In many cases, once an exit site is chronically infected, the catheter must be removed. The particulate ESM containing films as defined herein, by promoting wound repair and tissue growth around the exit site as well as inhibiting the growth of bacteria, would prolong the infection-free useful clinical life of a catheter, for example. Tissue in-growth onto the exterior of a catheter which has been coated with a particulate ESM-containing film as defined herein would effectively seal the path for potential infection through the exit site.

Thus, in a further aspect the invention provides an implantable medical device whose susceptible surfaces, or a portion thereof, e.g. percutaneous cuff, have been coated with a particulate ESM-containing film as defined herein.

In a further aspect of the invention there is provided a method for the delivery of particulate ESM to a wound, said method comprising applying a film or composite dressing or film coated implantable medical device as defined herein to said wound. Said delivery preferably results in the delivery of a uniform dose of ESM across the portion of the wound to which the film is applied, e.g. as a standalone entity or as part of a composite dressing or film coated implantable medical device as described herein. Said dose may be determined by the amount of particulate ESM provided in or on the film and the thickness of the film. The use of the films defined herein in such a method and the use of the films in the manufacture of a medicament, a composite dressing or film coated implantable medical device as described herein for use in such a method are specifically contemplated.

In further aspects the invention provides a method to promote the healing of a wound, wherein a film of the invention as defined herein is applied to said wound in an amount sufficient to promote the healing of the wound.

Alternatively, this aspect of the invention provides a film of the invention as defined herein for use in promoting the healing of wounds (or for use in a method to promote the healing of a wound).

Alternatively still, this aspect of the invention provides the use of a film of the invention as defined herein in the manufacture of a medicament for use in promoting the healing of wounds (or for use in a method to promote the healing of a wound).

In these aspects of the invention the film may be viewed as a pharmaceutical composition (or medicament) comprising particulate egg shell membrane (ESM) in the form of a dry biocompatible film comprising at least one film forming material and said ESM in which said ESM is distributed substantially uniformly in and/or on the film and wherein said film, or portion thereof, disintegrates upon contact with a wound or an exudate thereof.

The film may be used (applied or administered to the wound) on its own (at least initially at the point of contact with the wound) or as part of a composite dressing or film coated implantable medical device as described herein. In the following, reference to a film of the invention is also a reference to a composite dressing or film coated implantable medical device as described herein, unless context dictates otherwise.

By promotion of wound healing it is meant that the treatment of a wound with a film of the invention as defined herein accelerates the healing process of the wound in question (i.e. the progression of the wound through the three recognised stages of the healing process). The acceleration of the healing process may manifest as an increase in the rate of progression through one, two or all of the healing stages (i.e. the inflammatory stage, the proliferative stage and/or the remodelling phase). If the wound is a chronic wound that is stalled in one of the healing stages the acceleration might manifest as the restarting of the linear, sequential healing process after the stall. In other words, the treatment shifts the wound from a non-healing state to a state where the wound begins to progress through the healing stages. That progression after the restart may be at a normal rate or even a slower rate compared with the rate a normal acute wound would heal. Promotion of wound healing may also be considered to amount to the prevention of a deceleration the healing process of the wound in question. A deceleration of the healing process may manifest as a decrease in the rate of progression through one, two or all of the healing stages. If the wound is a chronic wound that is restarting of the linear, sequential healing process after a stall deceleration might manifest as a return to being stalled in one of the healing stages. In other words, the treatment prevents a wound from shifting from a healing state to a non-healing state. The promotion of wound healing may further be considered to amount to the treatment of an existing wound or the prevention of the growth of an existing wound and/or an existing healing wound becoming a poorly healing or chronic wound.

In this aspect the treatment of a wound with a film of the invention as defined herein in order to promote healing may reduce the activity of MMPs in a wound against ECM proteins and/or peptide growth or differentiation factors, or least may reduce the overall level of MMP activity or at least may reduce the level of ECM protein and/or peptide growth or differentiation factor degradation.

Accordingly the invention can be considered to encompass a method to promote the healing of a wound in which the activity of MMPs in the wound against ECM proteins and/or peptide growth or differentiation factors is reduced or limited, wherein a film of the invention as defined herein is applied to said wound in an amount sufficient to reduce or limit the activity of MMPs in a wound against ECM proteins and/or peptide growth or differentiation factors.

More generally the invention can be considered to encompass a method to promote the healing of a wound in which the overall level of activity of MMPs in the wound is reduced or limited, wherein a film of the invention as defined herein is applied to said wound in an amount sufficient to reduce or limit the overall level of activity of MMPs in a wound.

Also more generally the invention can be considered to encompass a method to promote the healing of a wound in which the degradation of ECM proteins and/or peptide growth or differentiation factors in the wound is reduced or limited, wherein a film of the invention as defined herein is applied to said wound in an amount sufficient to reduce or limit the degradation of ECM proteins and/or peptide growth or differentiation factors in the wound.

MMP-2 (also referred to as 72 kDa type IV collagenase or gelatinase A), MMP-8 (also referred to as neutrophil collagenase or PMNL collagenase) and/or MMP-9 (also referred to as 92 kDa type IV collagenase, 92 kDa gelatinase or gelatinase B) are commonly found in wounds, especially chronic wounds, and in preferred embodiments it is the activity of these MMPs specifically against ECM proteins and/or peptide growth or differentiation factors that is reduced.

In certain embodiments the activity of MMPs in a wound against ECM proteins and/or peptide growth or differentiation factors is reduced or limited to a level that is not detrimental to the healing process of wound undergoing treatment. This reduction may be observed as a reduction in the level of ECM protein (e.g. collagen and elastin) and/or peptide growth or differentiation factor fragments in the wound (or wound fluid), which in turn are an indication of the degradation of these proteins, and which may be detected by routine techniques including immunohistochemistry/immunocytochemistry techniques and/or biomolecule (e.g. protein) stains and dyes or by analysing wound fluid with chromatographic techniques. Limitation may be observed as the maintenance of such levels.

Each wound will require a different (e.g. reduced) level of MMP activity against ECM proteins and/or peptide growth or differentiation factors and even over time the requirements of the same wound in this regard may differ, however in most cases any reduction will be effective in promoting wound healing. While this may be determined by the skilled person without undue burden if necessary, a key advantage of the particulate ESM containing films disclosed herein is that it is relatively easy to achieve an effective level of MMP inhibition and as such onerous dose optimisation is not necessary as routine. Indeed, in most cases any reduction in MMP activity caused by the particulate ESM containing films defined herein will be effective in promoting wound healing.

Expressed numerically, following application of the film of the invention to the wound undergoing treatment, MMP activity against ECM proteins and/or peptide growth or differentiation factors in a wound (or overall ECM protein and/or peptide growth or differentiation factor degradation) will preferably be reduced by at least 5%, e.g. at least 10%, 15%, 20%, 25%, 30%. In certain embodiments it may be necessary to maintain some level of MMP activity against ECM proteins and/or peptide growth or differentiation factors (or overall ECM protein and/or peptide growth or differentiation factor degradation), and in such embodiment the reduction in MMP activity against ECM proteins and/or peptide growth or differentiation factors (or overall ECM protein and/or peptide growth or differentiation factor degradation) is no more than 90%, e.g. no more than 80%, 70%, 60%, 50%, 40%, 30%, 25%, 20%, 15%, 10% or 5%. Any and all range endpoints derivable from the combination of any of these values are specifically contemplated.

Without wishing to be bound by theory, the reduction or limitation in MMP activity against ECM proteins and/or peptide growth or differentiation factors (or overall ECM protein and/or peptide growth or differentiation factor degradation or overall MMP activity) may be on account of a number of mechanisms. This may include, but not be limited to, direct inhibition of the wound MMPs, absorption and deactivation of the wound MMPs, titrating out of the wound MMPs by providing alternative/excess substrate, inhibiting enzymes involved in wound MMP activation (e.g. serine proteases, including plasmin, neutrophil elastase and mast cell chymase), upregulating endogenous inhibitors of MMPs in the wound (e.g. TIMPs; tissue inhibitors of metalloproteinases) inhibiting the expression and/or secretion of MMPs by the cells of the wound and/or inflammatory cells, e.g. monocytes, macrophages, neutrophils and mast cells. The skilled person would be able to measure such effects in a wound without undue burden with routine analytical techniques, some of which are available commercially. The percentage reductions recited above apply in these contexts.

The reduction or limitation in MMP activity against ECM proteins and/or peptide growth or differentiation factors may be reflected in a reduction in or maintenance of overall MMP activity in the wound undergoing treatment. Overall MMP activity is a measure of all MMP activity against all wound substrates. Overall MMP activity can be measured without undue burden with routine analytical techniques, some of which are available commercially. Expressed numerically, following application of the film of the invention to the wound undergoing treatment overall MMP activity in the wound will preferably be reduced by at least about 5%, e.g. at least about 10%, 15%, 20%, 25%, 30%.

In certain embodiments it may be necessary to maintain some level of overall MMP activity, and in particular MMP activity against ECM proteins and/or peptide growth or differentiation factors, and in such embodiments the reduction in overall MMP activity, in particular MMP activity against ECM proteins and/or peptide growth or differentiation factors is no more than about 90%, e.g. no more than about 80%, 70%, 60%, 50%, 40%, 30%, 25%, 20%, 15%, 10% or 5%. Any and all combinations of range endpoints derivable from any of these values are specifically contemplated.

In other embodiments the overall activity of particular MMPs are considered, e.g. MMP-2, MMP-8 and/or MMP-9. In these embodiments overall MMP activity is the activity of the specific MMP in question against all wound substrates.

In one embodiment the method of this aspect of the invention may comprise a step in which the subject will be diagnosed as having a wound that is at risk of inappropriate, i.e. excessive, levels of MMP activity against ECM proteins and/or peptide growth or differentiation factors (or overall levels of MMP activity) or which would benefit from having MMP activity against ECM proteins and/or peptide growth or differentiation factors (or overall levels of MMP activity) reduced or limited (e.g. maintained). In other embodiments the method of this aspect of the invention may comprise a step in which the subject will be diagnosed as having a wound that is at risk of inappropriate, i.e. excessive, levels of ECM protein and/or peptide growth or differentiation factor degradation.

In a further embodiment, the method of this aspect of the invention may comprise, following application of the film of the invention to the wound, a step in which the degradation of ECM proteins and/or peptide growth or differentiation factors is monitored, and/or the MMP activity against ECM proteins and/or peptide growth or differentiation factors is monitored and/or overall MMP activity is monitored. In other embodiments MMPs 2, 8 and/or 9 are considered in place of MMPs in general.

Alternatively or additionally the method of the invention may comprise, following application of the film the invention to the wound, a step in which a clinical indicator of the wound (for example wound size (depth and/or area), healing time, general discomfort or pain in the wound or surrounding tissue) is monitored. These monitoring steps may involve comparison to the same metric immediately prior to application of the film of the invention to the wound or another point even earlier in the subject's treatment.

In this aspect a "sufficient (or effective) amount" of the film of the invention is that amount of film as defined herein which results in the effects on MMP activity and the degradation of ECM proteins and/or peptide growth or differentiation factors effects described above and thereby promotes the healing of the wound. The skilled man would easily be able to determine what an effective (sufficient) amount of the film of the invention would be on the basis of routine dose response protocols and, conveniently, the routine techniques for assessing MMP activity and the degradation of ECM proteins and/or peptide growth or differentiation factors discussed above. In other embodiments a "sufficient (or effective) amount" of the film of the invention is that amount of film as defined herein which results in positive effects on the clinical indicators of the wound described above.

The normal wound healing process involves an inflammatory stage, but in some instances the healing process becomes stuck in that inflammatory stage and the inflammatory response becomes excessive. As such, a wound healing treatment which may also deal with an excessive inflammatory response in the wound would be especially advantageous.

In this aspect the treatment of a wound with a film of the invention as defined herein in order to promote healing may reduce or limit inflammation in the wound. Accordingly the invention can be considered to encompass a method to promote the healing of a wound in which inflammation in the wound is reduced or limited, wherein a film of the invention as defined herein is applied to said wound in an amount sufficient to reduce or limit inflammation therein.

Inflammation in a wound may be seen as erythema, swelling, local warmth, odema and/or pus. A reduction in the anatomical extent and/or intensity of one or more of these signs of inflammation amounts to a reduction in inflammation. The maintenance of, or prevention of an increase in, the anatomical extent and/or intensity of one or more of these signs of inflammation amounts to a limitation in inflammation.

Alternatively, or in addition, the levels or activity of pro-inflammatory and/or anti-inflammatory markers, e.g. cytokines and chemokines, and/or immune cells in the wound may be measured, e.g. in a sample of wound tissue and/or in a sample from the wound interior. More specifically, the levels or activity of TNFα, IL-1, IL-6, NF-κB, ROS, histamine, macrophages, monocytes, mast cells and/or neutrophils may be measured. This may, for example, be by immunoassay or flow cytometry of a wound sample or suitable activity assays.

A reduction in the levels or activity of one or more pro-inflammatory markers and/or immune cells in the wound sample may be taken to amount to a reduction in inflammation in the wound. Similarly, an increase in the level or activity of one or more anti-inflammatory markers in a wound sample may be taken to amount to a reduction in the inflammation in a wound. The maintenance of, or prevention of an increase in, the level or activity of one or more pro-inflammatory markers and/or immune cells or maintenance of, or prevention of a decrease in, the level or activity of one or more the anti-inflammatory markers in the wound sample may be taken to amount to a limitation of the inflammation in the wound.

In this aspect a "sufficient (or effective) amount" of the film of the invention is that amount of film which results in the effects on the inflammation in a wound described above, in particular the effects on pro- and/or anti-inflammatory marker levels or activities and/or immune cell levels or activities, and thereby further promotes the healing of the wound. The skilled man would easily be able to determine what an effective (sufficient) amount of film would be on the basis of routine dose response protocols and, conveniently, the routine techniques for assessing wound inflammation, as discussed above.

In one embodiment the method of this aspect of the invention may comprise a step in which the subject will be diagnosed as having a wound that is at risk of developing inflammation or would benefit from having inflammation in it treated (i.e. reduced or limited).

In a further embodiment, the method of this aspect of the invention may comprise, following application of the film of the invention to the wound, a step in which the extent of the inflammation in the wound is monitored. These monitoring steps may involve comparison to the same metric immediately prior to application of the film of the invention to the wound or another point even earlier in the subject's treatment.

The normal wound healing process involves a proliferation stage in which the cells of the wound tissue migrate into the wound and/or proliferate to form de novo tissue, but in some instances the healing process becomes stuck in a preceding stage.

A wound healing treatment which may promote the viability and/or growth of the cells of the wound tissue would therefore be especially advantageous.

In this aspect the treatment of a wound with a film of the invention as defined herein in order to promote healing may promote the viability and/or growth of the cells of the wound tissue. Accordingly the invention can be considered to encompass a method to promote the healing of a wound in which the viability and/or growth of the cells of the wound tissue is promoted, wherein a film of the invention as defined herein is applied to said wound in an amount sufficient to promote the viability and/or growth of the cells of the wound tissue.

The term "viability and/or growth" should be interpreted consistently with the above discussion in the context of microorganisms (below), although in this instance growth may also include differentiation of the cells of the wound tissue.

By "promoting the growth of the cells of the wound tissue" it is meant that measurable growth (e.g. replication and/or differentiation) of the cells of the wound tissue, or the rate thereof, is increased or at least maintained or prevented from decreasing. Preferably measurable growth (e.g. replication and/or differentiation) of the cells of the wound tissue, or the rate thereof, is increased by at least 5%, more preferably at least 10%, 20%, 30% or 40%, e.g. at least 50%.

In one embodiment the method of this aspect of the invention may comprise a step in which the subject will be diagnosed as having a wound that would benefit from having the viability and/or growth of the cells of the wound tissue promoted.

In a further embodiment, the method of this aspect of the invention may comprise, following application of the film of the invention to the wound, a step in which the viability and/or growth of the cells of the wound tissue, and/or de novo tissue formation, is monitored. These monitoring steps may involve comparison to the same metric immediately prior to application of the film of the invention to the wound or another point even earlier in the subject's treatment.

A wound healing treatment which may promote the migration of the cells of the wound tissue into the wound would therefore also be especially advantageous.

In this aspect the treatment of a wound with a film of the invention as defined herein in order to promote healing may promote the migration of the cells of the wound tissue into the wound. Accordingly the invention can be considered to encompass a method to promote the healing of a wound in which the migration of the cells of the wound tissue into the wound is promoted, wherein a film of the invention as defined herein is applied to said wound in an amount sufficient to promote the migration of the cells of the wound tissue into the wound.

By "promoting migration" it is meant that measurable migration of the cells of the wound tissue into the wound, or the rate thereof, is increased or at least maintained or prevented from decreasing. Preferably measurable migration of the cells of the wound tissue, or the rate thereof, is increased by at least 5%, more preferably at least 10%, 20%, 30% or 40%, e.g. at least 50%.

In one embodiment the method of this aspect of the invention may comprise a step in which the subject will be diagnosed as having a wound that would benefit from having the migration of the cells of the wound tissue into the wound promoted.

In a further embodiment, the method of this aspect of the invention may comprise, following application of the film of the invention to the wound, a step in which the extent of the migration of the cells of the wound tissue into the wound, and/or de novo tissue formation, is monitored. These monitoring steps may involve comparison to the same metric immediately prior to application of the film of the invention to the wound or another point even earlier in the subject's treatment.

The promotion of migration and/or proliferation and/or differentiation may promote de novo tissue formation. The migration of the cells of the wound tissue into the wound, the proliferation and differentiation thereof and de novo tissue formation in the wound may be monitored and quantified by microscopic analysis of the wound or a sample thereof. Such analyses may involve chemical and/or immunochemical staining to detect molecular markers on the cells of the wound tissue and/or de novo tissue in the wound.

In these embodiments the wound cells will be contacted with the film of the invention following application of the film to the wound. More particularly the wound cells will be contacted with an effective amount of the film of the invention effective to promote the viability and/or growth of the cells of the wound tissue, promote the migration of the cells of the wound tissue into the wound or promote de novo tissue formation.

In these embodiments a "sufficient (or effective) amount" of the film of the invention as defined herein is that amount of film which results in the pro-proliferation or pro-migration effects described above, or which promotes de novo tissue formation, and thereby further promotes the healing of the wound. The skilled man would easily be able to determine what an effective (sufficient) amount of film would be on the basis of routine dose response protocols and, conveniently, the routine techniques for assessing wound cell viability, growth and migration discussed above.

Wounds are an ideal environment for infection, particularly chronic infection, due to their lack of an epithelial barrier and the availability of substrate and surface for microbial attachment and colonisation. Problematically, infection of a wound often delays healing, by increasing inflammation and necrosis in the wound and surrounding wound tissues, and thus renders that wound more susceptible to established (chronic) infection. Many wounds that struggle to heal comprise an infection and as such a wound healing treatment which may also deal with an infection in the wound (the so called bioburden of the wound) would be especially advantageous.

In this aspect the treatment of a wound with a film of the invention as defined herein in order to promote healing may inhibit the viability and/or growth of a microorganism present in the wound and thereby combat a microbial infection present in the wound. Accordingly the invention can be considered to encompass a method to promote the healing of a wound in which the viability and/or growth of a microorganism present in the wound is inhibited, or in which a microbial infection in the wound is combated, wherein a film of the invention as defined herein is applied to said wound in an amount sufficient to inhibit the viability and/or growth of the microorganism, or to combat the microbial infection.

The term "microorganism" as used herein includes any cellular microbial organism, that is any cellular organism that is microscopic, namely too small to be seen by the naked eye. In particular as used herein the term includes the organisms typically thought of as microorganisms, particularly bacteria, fungi, archaea, algae and protists. The microorganism may be prokaryotic or eukaryotic, and may be from any class, genus or species of microorganism. The microorganism may be aerobic or anaerobic. The microorganism may be pathogenic or non-pathogenic, or may be a spoilage or an indicator microorganism. The microorganism may be drug (i.e. antimicrobial drug, e.g. an antibiotic or an antifungal drug) resistant or multidrug resistant. In particular preferred embodiments the microorganism is capable of colonising a wound and delaying wound healing.

Bacteria or fungi represent preferred classes of microorganism and accordingly the films of the invention may be preferably viewed as having anti-bacterial or anti-fungal activity (e.g. bactericidal or bacteriostatic or fungicidal or fungistatic).

It is believed that it is not necessary for the films of the invention to recruit physiological systems or mechanisms (e.g. the immune system) to impart their microbicidal or microbiostatic (e.g. their cytotoxic or cytostatic) effects. Rather, the films of the invention (or at least the particulate ESM of the films) act directly on the microorganism.

Preferably the bacteria are selected from the following genera: *Achromobacter, Acinetobacter, Actinobacillus, Aeromonas, Agrobacterium, Alcaligenes, Alteromonas, Bacteroides, Bartonella, Borrelia, Bordetella, Brucella, Burkholderia, Campylobacter, Cardiobacterium, Chlamydia, Chlamydophila, Chromobacterium, Chyseobacterium, Chryseomonas, Citrobacter, Clostridium, Comamonas, Corynebacterium, Coxiella, Cryptobacterium, Edwardsiella, Eikenella, Enterobacter, Enterococcus, Erwinia, Kingella, Klebsiella, Lactobacillus, Lactococcus, Legionella, Leptospira, Leptotrichia, Leuconostoc, Listeria, Listonella, Mobiluncus, Moraxella, Morganella, Mycobacterium, Mycoplasma, Neisseria, Nocardia, Nocardiopsis, Pantoea, Parachlamydia, Pasteurella, Peptococcus, Peptostreptococcus, Prevotella, Propionibacterium, Proteus, Providencia, Pseudomonas, Ralstonia, Rickettsia, Salmonella, Shewenella, Shigella, Sphingobacterium, Sphingomonas, Staphylococcus, Stenotrophomonas, Streptobacillus, Streptococcus, Streptomyces, Treponem* and *Yersinia*.

Thus, the bacteria may be Gram positive or Gram negative bacteria, or indeed Gram-indeterminate bacteria. Gram-negative bacteria are of importance. Within the Gram-negative bacteria the Enterobacteriaceae and the Gram-negative bacteria non-fermenting bacteria are of particular note.

Preferably the bacteria may be selected from the genera *Pseudomonas, Acinetobacter, Burkholderia, Escherichia, Klebsiella, Streptococcus, Enterococcus, Providencia, Moraxalla, Staphylococcus*, e.g. *Pseudomonas aeruginosa, Acinetobacter baumannii, Burkholderia* spp, *E. coli, Klebsiella pneumoniae, Burkholderia cepacia, Burkholderia multivorans, Burkholderia mallei, Burkholderia pseudomallei, Acinetobacter Iwoffii, Providencia stuartii, Providencia rettgeri, Providencia alcalifaciens, Klebsiella oxytoca, Pseudomonas anguilliseptica, Pseudomonas oryzihabitans, Pseudomonas plecoglossicida, Pseudomonas luteola, Moraxalla catarrhalis, Enterococcus faecium, Enterococcus faecalis, Streptococcus oralis, Staphylococcus aureus* (e.g. MRSA).

The microorganism may also be a, or from a, fungus, including for example fungi that may be, or may have been, classified as protista, e.g. fungi from the genera *Candida, Aspergillus, Pneumocystis, Penicillium* and *Fusarium*. Representative fungal species include, but are not limited to, *Candida albicans, Candida dubliniensis, Cryptococcus neoformans, Histoplama capsulatum, Aspergillus fumigatus, Coccidiodes immitis, Paracoccidioides brasiliensis, Blastomyces dermitidis, Pneomocystis carnii, Penicillium marneffi, Alternaria alternate*.

The microorganism may be in a biofilm, or put differently, the microorganism may be in a biofilm mode of growth. By "biofilm" it is meant a community of microorganisms characterized by a predominance of sessile cells that are attached to a substratum or interface or to each other (some motile cells may also be present) and that are embedded in a matrix of extracellular polymers (more specifically extracellular polymers that they have produced) characterised in that the microorganisms of this colony exhibit an altered phenotype with respect to growth rate and gene transcription (for example as compared to their "non-biofilm" or free-floating or planktonic counterparts). By "in a biofilm" it is meant that the microorganism is within (completely or in part), on or associated with the polymer matrix of a biofilm. Viewed differently, microorganisms that are "not in a biofilm" are microorganisms that are either in isolation, e.g. planktonic, or if in an aggregation of a plurality of microorganisms, that aggregation is unorganised and/or is devoid of the matrix characteristic of a biofilm. In each case, the individual microorganisms do not exhibit an altered phenotype that is observed in their biofilm dwelling counterparts.

The term "viability of a microorganism" means the ability of a microbe to survive under given conditions, e.g. in a wound. Survival can be considered equivalent to remaining alive. The films of the invention may reduce the viability of microorganisms through a microbicidal effect. Determining the viability of a microorganism can be done using the techniques detailed below for measuring microorganism cell death (and viability).

Thus, "inhibiting the viability" of a microorganism can include any effect which reduces the viability of a microorganism, or which renders it less likely to survive, or non-viable. In particular this term covers killing or destroying a microorganism.

The term "killing a microorganism" refers to the act of causing a microorganism to cease to be alive, i.e. to become dead. A microorganism is considered to be alive if it can be induced to replicate and/or grow, or at least display morphological changes, when placed in a medium that would normally support the growth of that microorganism and/or the microorganism is metabolising nutrients to release energy to support cellular functions. Typically, a microorganism can be considered to be dead if cell membrane integrity is lost.

Many routine assays are available to determine if a microorganism is alive (viable) or dead. One option is to place the microorganism in conditions that would normally support the growth of that microorganism and monitor the growth of the microorganism by appropriate standard means, e.g. by monitoring the size of the microorganism, the morphology of the microorganism, the number of microorganisms in the colony over time, the consumption of nutrients in the culture media, etc. Another option is to assess the microorganism for morphologies characteristic of cell death, e.g. necrotic or apoptotic bodies, membrane blebs, nuclear condensation and cleavage of DNA into regularly sized fragments, ruptured cell walls or membranes and leakage of cell contents into the extracellular environment. Other methods exploit the characteristic loss of cell membrane integrity in dead microorganisms. Membrane impermeable dyes (e.g. trypan blue and propidium iodide) are routinely used to assess membrane integrity. A still further option is to measure the metabolism of the microorganism. This can be done routinely in a number of ways. For instance the levels of ATP can be measured.

By "growth of a microorganism" it is meant both an increase in the size of the microorganism or in the amount and/or volume of the constituents of a microorganism (e.g. the amount of nucleic acid, the amount of protein, the number of nuclei, the numbers or size of organelles, the volume of cytoplasm) and an increase in the numbers of a microorganism i.e. an increase in the replication of a microorganism.

By "inhibiting the growth of a microorganism" it is meant that measurable growth (e.g. replication) of a microorganism, or the rate thereof, is reduced. Preferably measurable growth (e.g. replication) of a microorganism, or the rate thereof, is reduced by at least 50%, more preferably at least 60%, 70%, 80% or 90%, e.g. at least 95%. Preferably, measurable growth (e.g. replication) is ceased. Growth in terms of microbial size increase or expansion etc. may be inhibited independently of replication and vice versa. The films of the invention may inhibit the viability of microorganisms through a microbistatic effect and/or a microbicidal effect.

These aspects of the invention can also be seen to provide a film of the invention as defined herein for use in combating, and in particular in the treatment of, microbial infection in a wound, or the use of a film of the invention as defined herein in the manufacture of a medicament for use in combating, and in particular in the treatment of, microbial infection in a wound. It will be seen in this aspect that the infection may be combated by inhibiting the growth and/or viability of a microorganism in a subject. The infection may be a biofilm infection.

"Combating an infection" can be viewed as the treatment or prevention of infection, e.g. including the prevention or inhibition of formation of an infection, the reduction or elimination of an infection, a reduction in the number of microbes in the colony making up the infection, a reduction or cessation in the rate of growth of the infection and/or the microorganisms therein, a reduction in or cessation of the rate of expansion in the number of microbes in an infection. "Combating biofilm" includes both preventative and reactionary measures or treatments. Combating biofilm therefore encompasses the prevention or inhibition of formation of a biofilm, the elimination or reduction of a biofilm, a reduction in biofilm size, a reduction in the number of microbes in a biofilm colony, a reduction or cessation in the rate of growth of a biofilm, a reduction in or cessation of the rate of expansion in the number of microbes in a biofilm colony, a reduction in the physical integrity of a biofilm, an increase in the sensitivity of the microbes in a biofilm colony to an anti-microbial agent or host immune defence mechanism and an increase in the permeability of a biofilm to an anti-microbial agent or host immune defence mechanism.

In these embodiments the microorganism will be contacted with the film of the invention as defined herein following application of the film to the wound. The term "contacting" encompasses applying the film directly to a microorganism which is already present in or on the wound, or applying the film to a wound to which the microorganism later comes into contact.

More particularly the microorganism will be contacted with an effective amount of the film of the invention, more particularly an amount of the film of the invention effective directly to inhibit the viability of (e.g. to kill) the microorganism or to inhibit directly the growth of the microorganism.

By "directly" it is meant that it is the film of the invention does not recruit physiological systems or mechanisms (e.g. the immune system) to impart their microbicidal or microbiostatic (e.g. their cytotoxic or cytostatic) effects. Rather, the film of the invention acts directly on the microorganism.

In these embodiments a "sufficient (or effective) amount" of the film of the invention is that amount of film which results in the microbicidal or microbiostatic effects described above, or which effectively combats infection, and thereby promotes the healing of the wound. The skilled man would easily be able to determine what an effective (sufficient) amount of film would be on the basis of routine dose response protocols and, conveniently, the routine techniques for assessing microbial death or growth inhibition etc., as discussed above. The direct effects of the film of the invention can be assessed by using routine in vitro systems familiar to the skilled man which are devoid of complete physiological systems or mechanisms that may interfere with the assessment of microbicidal or microbiostatic effects (e.g. simple cell culture systems, isolated cell/virus systems).

In one embodiment the method of this aspect of the invention may comprise a step in which the subject will be diagnosed as having a wound that is at risk of developing an infection or would benefit from having infection in it treated.

In a further embodiment, the method of this aspect of the invention may comprise, following application of a film of the invention as defined herein to the wound, a step in which the growth and/or viability of a microorganism in the wound or the extent of infection is monitored. These monitoring steps may involve comparison to the same metric immediately prior to application of the film of the invention to the wound or another point even earlier in the subject's treatment.

In certain embodiments the methods of the invention achieve the promotion of wound healing with two or more, or all, of the above described wound effects, e.g. the inhibition of the degradation of ECM and/or peptide growth or differentiation factors (in particular the inhibition of MMP activity against ECM and/or peptide growth or differentiation factors) and one or more of the above described wound effects, in particular the anti-inflammatory effects, but also the promotion of proliferation, migration and/or differentiation of the cells of the wound tissue and/or de novo tissue formation and/or the antimicrobial effect.

In certain embodiments the methods of the invention achieve the promotion of wound healing with either (i) the inhibition of the degradation of ECM and/or peptide growth or differentiation factors (in particular the inhibition of MMP activity against ECM and/or peptide growth or differentiation factors) and one or more, or all, of the above described additional wound effects, in particular the antimicrobial effect and/or the anti-inflammatory effects; or (ii) the reduction in inflammation in the wound and one or more, or all, of the above described additional wound effects, in particular the antimicrobial effect and/or the MMP inhibition effects.

The wound may be found in or on a subject. The term "in a subject" is used broadly herein to include sites or locations inside a subject or on a subject, e.g. an external body surface, and may include in particular a wound containing an implantable a medical device.

Thus, the wound may therefore be found in or on the skin or in or on any susceptible surface in the oral cavity (e.g. gingiva, gingival crevice, periodontal pocket), the reproductive tract (e.g. cervix, uterus, fallopian tubes), the peritoneum, the gastrointestinal tract, the ear, the eye, the prostate, the urinary tract, the vascular system, the respiratory tract, the heart, the kidney, the liver, the pancreas, the nervous system or the brain. The "cells of the wound tissue" should be interpreted accordingly. Preferably the wound is a skin (cutaneous) wound, in other words a dermal or dermatological wound, which includes wounds to any depth of the epidermis and/or dermis and the underlying tissue.

Implantable medical devices include, but are not limited to, any kind of percutaneous devices and/or line which results in a wound (e.g. central venous catheters, in particular catheters with cuffs, e.g. Dacron or collagen cuffs), prosthetic devices, e.g., heart valves, artificial joints, dental implants and soft tissue implants (e.g. breast, buttock and lip implants), stents, pacemakers, and tracheostomy tubes. An "implantable" medical device may include a device in which any part of it is contained within the body, i.e. the device may be wholly or partly implanted.

Wounds may be caused surgically, by physical injury (e.g. mechanical injuries; thermal injuries, for instance those resulting from excessive heat or cold; electrical injuries, for instance those caused by contact with sources of electrical potential; and radiation damage caused, for example, by prolonged, extensive exposure to infrared, ultraviolet or ionizing radiations) or by a spontaneously forming lesion such as a skin ulcer (e.g. a venous, diabetic or pressure ulcer), an anal fissure, a mouth ulcer and acne vulgaris. Surgically grafted tissue is considered to be a wound.

In the field of medicine, wounds are typically defined as either acute or chronic. Acute wounds are wounds that proceed orderly through the three recognised stages of the healing process following haemostasis (i.e. the inflammatory stage, the proliferative stage and the remodelling phase) without a protracted timecourse. Chronic wounds are defined as those which fail to heal or where there is excessive skin loss such as through burns. Such wounds do not complete the ordered sequence of biochemical events of the healing process because the wound becomes stalled in one of the healing stages. Commonly, chronic wounds are stalled in the inflammatory phase. Chronic wounds are a major source of morbidity for patients.

In accordance with a particular aspect of the present invention, a chronic wound may be considered to be a wound that has not healed in the expected amount of time, e.g. at least 5, 10, 15, 20 or 30 days longer than expected. This may be taken as a wound which has not healed within at least 30, at least 40 days, particularly at least 50 days, more particularly at least 60 days, most particularly at least 70 days.

Also of particular note are burn wounds. Any burn, in particular a severe burn, has a significant impact on the integrity of the epithelial and/or endothelial barrier of the subject and the healing of such traumas is often a lengthy process.

As such, the methods of the invention may be considered to be methods for the promoting the healing of a burn.

Typical burn-causing agents are extremes of temperature (e.g. fire and liquids and gases at extreme temperature), electricity, corrosive chemicals, friction and radiation. The extent and duration of exposure, together with the intensity/strength of the agent, result in burns of varying severity. Scalding (i.e. trauma associated with high temperature liquids and/or gases) is considered to be a burn.

In certain embodiments the wound is a wound at risk of, or in which there is, an inappropriate, i.e. excessive, level of MMP, e.g. MMP-2, MMP-8 and/or MMP-9, activity against ECM proteins and/or peptide growth or differentiation factors. In other embodiments the wound is a wound at risk of, or in which there is, an inappropriate, i.e. excessive, level of overall MMP activity. In other embodiments the wound is a wound at risk of, or in which there is, an inappropriate, i.e. excessive, level of ECM and/or peptide growth or differentiation factor degradation. Wounds with these features may be identified with the above described methods for measuring ECM protein and/or peptide growth or differentiation factor degradation or for monitoring overall or specific MMP activity against ECM proteins and/or peptide growth or differentiation factors or wound substrates in general.

In certain embodiments the wound is a wound at risk of becoming, or which is, inflamed, e.g. a wound which contains immune cells (e.g. macrophages, monocytes, mast cells and/or neutrophils) and/or inappropriate, i.e. excessive, levels of pro-inflammatory markers (e.g. those disclosed herein) and/or inappropriate, i.e. insufficient, levels of anti-inflammatory markers (e.g. those disclosed herein).

In certain embodiments the wound is a wound at risk of, or which there is, inappropriate, i.e. insufficient, levels of wound tissue cell migration into the wound and/or proliferation or differentiation of wound tissue cells and/or de novo tissue formation.

In certain embodiments the wound is a wound at risk of, or which contains, a microbial infection, e.g. those disclosed herein. The infection may be acute, or alternatively chronic, e.g. an infection that has persisted for at least 5 or at least 10 days, particularly at least 20 days, more particularly at least 30 days, most particularly at least 40 days.

In still further embodiments the wound has two or more, or all, of the above described wound features, e.g. MMP overactivity (in particular against ECM and growth factors) or excessive ECM and growth factor degradation and one or more of the above described wound features, in particular, inflammation but also infection and/or insufficient levels of wound tissue cell migration into the wound and/or proliferation or differentiation of wound tissue cells and/or de novo tissue formation.

In still further embodiments the target wound has either (i) MMP overactivity (in particular against ECM and growth factors) or excessive ECM and growth factor degradation and one or more of the other above described wound features, in particular microbial infection and inflammation; or (ii) excessive inflammation and one or more of the other above described wound features, in particular microbial infection and MMP overactivity (in particular against ECM and growth factors) or excessive ECM and growth factor degradation.

The subject may be any human or non-human animal subject, but more particularly may be a human or non-human vertebrate, e.g. a non-human animal selected from mammals, birds, amphibians, fish and reptiles. The non-human animal may be a livestock or a domestic animal or an animal of commercial value, including laboratory animals or an animal in a zoo or game park. Representative non-human animals therefore include dogs, cats, rabbits, mice, guinea pigs, hamsters, horses, pigs, sheep, goats, cows, chickens, turkeys, guinea fowl, ducks, geese, parrots, budgerigars, pigeons, salmon, trout, tilapia, catfish, bream, barramundi, grouper, mullet, amberjack, croaker, rohu, goby, cod, haddock, sea bass and carp. Veterinary uses of the invention are thus covered. The subject may be viewed as a patient. Preferably the subject is a human.

"Treatment" when used in relation to the treatment of a medical condition (e.g. a wound) or infection in a subject in accordance with the invention is used broadly herein to include any therapeutic effect, i.e. any beneficial effect on the condition or in relation to the infection. Thus, not only included is eradication or elimination of the condition/infection, or cure of the subject of the condition/infection, but also an improvement in the infection/condition of the subject. Thus included for example, is an improvement in any symptom or sign of the infection/condition, or in any clinically accepted indicator of the infection/condition (for example a decrease in wound size (depth and/or area), an acceleration of healing time, one or more of the wound effects described herein, or a reduction in general discomfort or pain in the wound or surrounding tissue). Treatment thus includes both curative and palliative therapy, e.g. of a pre-existing or diagnosed infection/condition, i.e. a reactionary treatment.

"Prevention" as used herein refers to any prophylactic or preventative effect. It thus includes delaying, limiting, reducing or preventing the condition (e.g. an increase in the size of the wound or the development of a chronic or poorly healing wound) or infection or the onset of the condition/infection, or one or more symptoms or indications thereof, for example relative to the condition/infection or symptom or indication prior to the prophylactic treatment. Prophylaxis thus explicitly includes both absolute prevention of occurrence or development of the condition/infection, or symptom or indication thereof, and any delay in the onset or development of the condition/infection or symptom or indication, or reduction or limitation on the development or progression of the condition/infection or symptom or indication.

Specifically, a film of the invention as defined herein can be used as a prophylactic treatment, for example to prevent, or at least minimise the risk of, wound infection or to prevent, or at least minimise the risk of, an increase in wound size or development of a poorly healing or chronic wound.

The invention will be further described with reference to the following non-limiting Examples in which:

BRIEF DESCRIPTION OF THE DRAWING

FIG. 1 shows the effect of a disintegratable ESM-containing collagen film compared with recombinant growth factors on wound healing in a diabetic mouse model. Positive control (growth factors): triangles; negative control: squares; ESM film: diamonds. All groups: mean±s.e.m.

EXAMPLES

Example 1—Preparation of Collagen-ESM and Gelatin-ESM Dry Disintegratable Films

Eggshell membrane was prepared in accordance with WO 2015058790 and then ground into fine particles using a rotational blade mill.

Collagen suspensions were prepared by adding either 1 or 2 g of bovine dermal collagen to 200 mL of 0.5M acetic acid (0.5 to 1 wt % suspensions). These suspensions were mixed using an overhead blender (Ultra Turrax, IKA Works) for 15 minutes in a cooled (7° C.) reaction vessel. ESM powder (2 to 12 g, 1 to 6 wt %) was then added to the suspension and mixed for a further 15 minutes. By this method, a range of ratios of collagen:ESM mixtures were prepared.

Gelatin suspensions were prepared by adding 20 g of gelatin to 200 mL of 0.5 M acetic acid (10 wt % suspension) which was heated to 40° C. on a hot plate and stirred using a magnetic stirrer for 20 min. ESM powder (6 g, 3 wt %) was then added to the suspension and mixed for a further 15 minutes.

The ESM-[collagen/gelatin] suspensions were poured directly onto plastic acetate sheets with a raised edge to prevent run-off and to be able to modify the thickness of the final dried film. These were then dried at 37° C. in a drying oven. The films were then gamma irradiated (25 kGy) for sterilization.

Example 2—Properties of Collagen-ESM and Gelatin-ESM Dry Disintegratable Films

The films of Example 1 in the range of 1:1 to 1:6 ESM:collagen or ESM:gelatin were assessed for physical properties. 1:1 films were found to be more manageable with better handling characteristics than 1:6 films. 1:3 collagen films were found to be robust and to have an optimal solubilisation profile.

The amount of ESM per cm$^2$ was varied by modifying the depth of mixture in the acetate sheet mould. ESM-[collagen/gelatin] suspensions can be poured to depths of 1 mm to 5 mm. For a 1:6 ESM:collagen or ESM:gelatin film this corresponds to 3 mg ESM cm$^2$ to 15 mg ESM cm$^2$ and a final thickness of dry film of 0.2 mm to 1 mm. A film made with a 1:6 ESM:collagen ratio corresponding to 3 mg ESM cm$^2$ in the final dried film (0.2 mm) was optimal. This provided a robust film with appropriate handling characteristics, an adequate solubility profile and an effective concentration of ESM particles for delivery and release to the wound surface.

Example 3—Assessment of Dry Disintegratable ESM-Containing Film in Pre-Clinical Effectiveness Model The effectiveness of the 1:3 collagen ESM film of Example 1 and 2 was shown in the diabetic db/db mouse model of delayed wound healing. In this model, a 1 cm$^2$ full skin thickness section was excised from the dorsal region. The wound was then covered with a simple protective transparent dressing and decrease in wound area was assessed over time relative to controls. The positive control was the active ingredient of Regranex™, a recombinant human platelet derived growth factor based wound healing drug product. The model is challenging for a medical device as the control is a pharmacologically active material which represents maximum wound healing achievable within the model over 20 days.

The healing response of wounds treated with this film formulation was compared to that of wounds exposed to (i) 'no treatment' (negative control) and (ii) positive control treatment (platelet-derived growth factor-BB [rh-PDGF-BB]+Transforming Growth Factor-alpha [rh-TGF-α]). In all cases, the wounds were covered post treatment with a transparent dressing, the Bioclusive Film Dressing (BFD), which provided a sterile barrier and protected the wound from infection and physical damage and irritation. The groups are shown in Table 1. The positive control was dosed daily for 6 days at the start of treatment and the ESM film was applied on days 0 and 4.

TABLE 1

Details of treatment groups used in study

| Tx Group | Treatment (BFD = Bioclusive Film Dressing) | Group name |
|---|---|---|
| 1 | BFD only | Negative control |
| 2 | ESM Film + BFD | ESM-Film |
| 3 | rh-PDGF-BB [10 µg] + rh-TGF-α [1 µg] + BFD | Positive control |

The area of a given wound, at a given time point, was expressed as a percentage of the area of that wound immediately after injury (i.e. day 0). The mean percentage wound area remaining (& standard error of mean) was calculated for each group and was displayed graphically. Results are shown in FIG. 1.

The following were shown:

1) Wound closure profiles were found to differ noticeably between the different treatment groups. Wounds in receipt of the growth factor combination (positive control) were found to display the fastest rate of closure—demonstrating close to full wound closure by day 16 post-wounding and significantly greater levels of wound closure relative to untreated wounds from day 8 onwards the study period (p=0.000, Mann-Whitney U test).
2) ESM film treatment resulted in significantly increased wound closure relative to 'no treatment'—from day 8 onwards (p≤0.034, Mann-Whitney U test)
3) The effect of the ESM lags behind that of the PDGF/TGF positive control by approximately 4 days.
4) The effect shown with the ESM film is equivalent to that achieved with ESM powder at the same dosage and dosing frequency (data not shown), demonstrating that the collagen carrier is not having a negative effect on the potency of the ESM material in wound healing.

In conclusion, ESM films of the invention have comparable activity to PDGF based products and the lag in wound healing response is acceptable in the light of reduced concerns of a cancer associated with use of growth factors. Together with the fact that ESM films are easy to apply and may be used with any secondary occlusive dressing currently available, such film represent a cost effective alternative to pharmacologically active wound healing products.

Example 4—Carboxymethylcellulose Based Dry Disintegratable Film

| | % dry w/w |
|---|---|
| Carboxymethylcellulose | 80-90 (representative 88%) |
| Glycerol | 2-4 (representative 2%) |
| Particulate ESM | 6-18 (representative 10%) |

Example 5—Hydroxypropylcellulose Based Dry Disintegratable Film

| | % dry w/w |
|---|---|
| Hydroxypropylcellulose e | 80-90 (representative 84%) |
| Glycerol | 2-4 (representative 3%) |
| Particulate ESM | 6-18 (representative 13%) |

Example 4—Hydroxyethylcellulose Based Dry Disintegratable Film

| | % dry w/w |
|---|---|
| Hydroxyethylcellulose | 80-90 (representative 82%) |
| Glycerol | 2-4 (representative 4%) |
| Particulate ESM | 6-18 (representative 14%) |

The invention claimed is:

1. A dry biocompatible film comprising at least one film forming material and particulate egg shell membrane (ESM), wherein
   (i) said film does not have a knitted, woven or felted structure, said particulate ESM is distributed uniformly in the film and said film, or portion thereof, disintegrates upon contact with a wound or an exudate thereof, (ii) said at least one film forming material is a cellulose which is not in insoluble fibrous or filamentous form, and (iii) said particulate ESM is, or is formed from, at least one particle of ESM having a mean particle diameter of less than 100 µm, and is free from egg shell.

2. The dry biocompatible film of claim 1, wherein the film forming material of the film is dissolvable in water and other aqueous liquids.

3. The dry biocompatible film of claim 1, wherein the film degrades and/or is degraded upon contact with a wound component.

4. The dry biocompatible film of claim 3, wherein said wound component is an enzyme, an inflammatory cell, a wound cell, a wound microorganism, a salt, or a reactive oxygen species.

5. The dry biocompatible film of claim 4, wherein:
(i) the enzyme is selected from a matrix metalloproteinase, collagenase, elastase, and chymase,
(ii) the inflammatory cell is selected from a macrophage, a neutrophil, and a monocyte.

6. The dry biocompatible film of claim 1, wherein said cellulose is selected from oxidised regenerated cellulose, hydroxyethylcellulose, hydroxypropylcellulose and carboxymethylcellulose.

7. The dry biocompatible film of claim 1, wherein upon contact with a wound or exudate thereof, said film disintegrates in about 3 to about 25 minutes.

8. The dry biocompatible film of claim 1, wherein the film comprises
(i) about 5% to about 95% w/w particulate ESM, the remainder being made up of said at least one film forming material and optionally further excipients or active agents; or
(ii) about 5% to about 95% w/w of said at least one film forming material, the remainder being made up of particulate ESM and optionally further excipients or active agents.

9. The dry biocompatible film of claim 1, wherein said particulate ESM and the at least one film forming material are present at a ratio of 1:19 to 19:1 ESM:film forming material.

10. The dry biocompatible film of claim 1, wherein said film consists essentially of particulate ESM, a cellulose derivative selected from hydroxyethylcellulose, hydroxypropylcellulose, carboxymethylcellulose, and mixtures thereof and, optionally, a plasticiser.

11. The dry biocompatible film of claim 10, wherein the ESM and cellulose derivative are present at ratios of 1:19 to 1:1.

12. The dry biocompatible film of claim 1, wherein said film is bioadhesive.

13. The dry biocompatible film of claim 1, wherein said particulate ESM is essentially spherical, prismatoidal, cylindrical, rod-shaped, needle-shaped or fibrous.

14. The dry biocompatible film of claim 13, wherein said particulate ESM has an aspect ratio between a first length dimension and a second length dimension arranged perpendicular thereto of at least 1.5 first length dimension:second length dimension.

15. The dry biocompatible film of claim 1, wherein said ESM is ESM of the eggs of *Gallus gallus domesticus*.

16. The dry biocompatible film of claim 1, wherein said film further comprises a clinically-useful anti-microbial agent, a growth factor, or an anti-inflammatory agent.

17. A method for preparing a dry biocompatible film as defined in claim 1, said method comprising
(i) providing particulate ESM and said at least one film forming material in a liquid suspension, and
(ii) drying the suspension, optionally in a mould or on a flat surface, thereby obtaining said film.

18. A method for preparing a dry biocompatible film as defined in claim 1, said method comprising
(i) providing a dry biocompatible film formed from at least one film forming material, wherein said film, or portion thereof, disintegrates upon contact with a wound or an exudate thereof, and
(ii) applying particulate ESM uniformly to at least one surface of the film.

19. A dry biocompatible film comprising at least one film forming material and particulate ESM obtained or obtainable by the method of claim 17.

20. A composite wound dressing comprising a dry biocompatible film as defined in claim 1 and a further wound dressing adapted such that the film is exposed to the wound or wound exudate when in use.

21. An implantable medical device whose susceptible surfaces, or a portion thereof, carry a dry biocompatible film as defined in claim 1.

22. A method for the delivery of particulate ESM to a wound, said method comprising applying a dry biocompatible film as defined in claim 1 to said wound.

23. A method to promote the healing of a wound, wherein a dry biocompatible film as defined in claim 1 is applied to said wound in an amount sufficient to promote the healing of the wound.

* * * * *